(12) United States Patent
Ogbourne et al.

(10) Patent No.: US 8,106,092 B2
(45) Date of Patent: Jan. 31, 2012

(54) TREATMENT OF SOLID CANCERS

(75) Inventors: Steven Martin Ogbourne, Bunya (AU); Andreas Suhrbier, Bunya (AU)

(73) Assignee: LEO Laboratories Limited, Dublin (IE)

( * ) Notice: Subject to any disclaimer, the term of this patent is extended or adjusted under 35 U.S.C. 154(b) by 0 days.

(21) Appl. No.: 11/792,264

(22) PCT Filed: Dec. 2, 2005

(86) PCT No.: PCT/AU2005/001827
§ 371 (c)(1),
(2), (4) Date: Sep. 25, 2007

(87) PCT Pub. No.: WO2006/063382
PCT Pub. Date: Jun. 22, 2006

(65) Prior Publication Data
US 2008/0187513 A1    Aug. 7, 2008

(30) Foreign Application Priority Data
Dec. 13, 2004   (AU) ................................ 2004907105

(51) Int. Cl.
*A01N 37/00* (2006.01)
(52) U.S. Cl. ........................................... 514/529; 514/1
(58) Field of Classification Search .................. None
See application file for complete search history.

(56) References Cited

U.S. PATENT DOCUMENTS

| | | | |
|---|---|---|---|
| 3,809,749 A | 5/1974 | Paersinos | |
| 4,418,064 A | 11/1983 | Powell et al. | |
| 4,560,774 A | 12/1985 | Pettit et al. | |
| 4,716,179 A | 12/1987 | Hecker et al. | |
| 5,145,842 A | 9/1992 | Driedger et al. | |
| 5,643,948 A | 7/1997 | Driedger et al. | |
| 5,716,968 A | 2/1998 | Driedger et al. | |
| 5,750,568 A | 5/1998 | Driedger et al. | |
| 5,874,464 A | 2/1999 | Marquez et al. | |
| 5,886,017 A | 3/1999 | Driedger et al. | |
| 5,886,019 A | 3/1999 | Driedger et al. | |
| 5,891,870 A | 4/1999 | Driedger et al. | |
| 5,891,906 A | 4/1999 | Driedger et al. | |
| 5,932,613 A | 8/1999 | Jiang et al. | |
| 5,962,498 A | 10/1999 | Driedger et al. | |
| 6,432,452 B1 | 8/2002 | Aylward | |
| 6,787,161 B2 | 9/2004 | Aylward | |
| 6,844,013 B2 | 1/2005 | Aylward | |
| 7,378,445 B2 * | 5/2008 | Aylward et al. | 514/549 |
| 7,410,656 B2 | 8/2008 | Aylward | |
| 7,449,492 B2 | 11/2008 | Aylward et al. | |
| 2003/0171334 A1 | 9/2003 | Aylward et al. | |
| 2003/0171337 A1 | 9/2003 | Aylward et al. | |
| 2003/0195168 A1 | 10/2003 | Aylward et al. | |
| 2005/0209192 A1 | 9/2005 | Aylward et al. | |
| 2007/0020297 A1 * | 1/2007 | Wheeler et al. | 424/277.1 |

FOREIGN PATENT DOCUMENTS

| | | |
|---|---|---|
| CN | 1077129 | 10/1993 |
| CN | 1105246 | 7/1995 |
| CN | 1112011 | 11/1995 |
| CN | 1131037 | 9/1996 |
| DE | 29 02 506 | 7/1980 |
| DE | 41 02 054 A1 | 7/1992 |
| EP | 0 310 622 B1 | 4/1989 |
| EP | 0 330 094 A1 | 8/1989 |
| EP | 0 455 271 B1 | 11/1991 |
| JP | 8-13571 | 1/1996 |
| JP | 8-176002 | 7/1996 |
| JP | 8-245505 | 9/1996 |
| WO | WO 87/07599 | 12/1987 |
| WO | WO 97/15575 | 5/1997 |
| WO | WO 99/08994 | 2/1999 |
| WO | WO 02/11743 * | 2/2002 |
| WO | WO 02/11743 A2 | 2/2002 |
| WO | WO 2005/065696 A1 | 7/2005 |
| WO | WO 2006/063382 A1 | 6/2006 |
| WO | WO 2007/053912 A1 | 5/2007 |
| WO | WO 2007/059584 A1 | 5/2007 |
| WO | WO 2007/068963 A2 | 6/2007 |
| WO | WO 2008/131491 A1 | 11/2008 |

OTHER PUBLICATIONS

Gura, Science, 1997, 278:1041-1042).*
Salah et al, J. Cancer Res Clin Oncol, 1998, 124:131-140).*
Granziero et al, Eur. J. Immunol. 1999, 29:1127-1138.*
Byers, CA Journal, vol. 49, No. 6, Nov./Dec. 1999.*
Ogbourne S. M. et al., "Antitumour Activity of 3-Ingenyl Angelate: Plasma Membrane and Mitochondrial Disruption and Necrotic Cell Death", *Cancer Research* 64:2833-2839 (2004).
Ogbourne S.M. et al., "Proceedings of the First International Conference on PEP005", *Anti-Cancer Drugs* 18(3):357-362 (2007).
Tropical Plant Database, Database File for AVELOZ (*Euphorbia tirucalli*), http://web.archive.org/web/20041030080015/http://www.rain-tree.com/aveloz.htm (2007).
Bhatt V.P. et al., "Ethnomedicinal Plant Resources of *Jaunsari* Tribe of Garhwal Himalaya, Uttaranchal", *Indian Journal of Traditional Knowledge* 5(3):331-335 (2006).
Jadeja B.A. et al., "Indigenous Animal Healthcare Practices in District Porbandar, Gujarat", *Indian Journal of Traditional Knowledge* 5(2):253-258 (2006).
Jeeva S. et al., "Weeds of Kanyakumari District and Their Value in Rural Life", *Indian Journal of Traditional Knowledge* 5(4):501-509 (2006).

(Continued)

*Primary Examiner* — Misook Yu
*Assistant Examiner* — Mark Halvorson
(74) *Attorney, Agent, or Firm* — Edwards Wildman Palmer LLP

(57) ABSTRACT

The present invention relates generally to the field of cancer including tumor therapy. More particularly, the present invention relates to the treatment of solid cancers, including solid tumors, and the prevention or reduction of cancer metastasis, by chemoablation of cancer cells by an agent which also stimulates the generation of cancer-specific T-cells, a process referred to herein as immunostimulatory chemoablation. The present invention further contemplates combination therapy comprising immunostimulatory chemoablation and one or more other therapeutic regimens, which enhance, co-operate and/or synergize with the cancer-specific T-cells induced by the chemoablation. The present invention also relates to pharmaceutical compositions for use in treating cancers.

14 Claims, 11 Drawing Sheets

OTHER PUBLICATIONS

Katewa S.S. et al., "Traditional Herbal Medicines from Shekhawati Region of Rajasthan", *Indian Journal of Traditional Knowledge* 4(3):237-245 (2005).

Hampson P. et al., "PEP005, a Selective Small-Molecule Activator of Protein Kinase C, has Potent Antileukemic Activity Mediated Via the Delta Isoform of PKC", *Blood* 106(4):1362-1368 (2005).

Jain S.K. et al., "Traditional Uses of Some Indian Plants Among Islanders of the Indian Ocean", *Indian Journal of Traditional Knowledge* 4(4):345-357 (2005).

Natarajan D. et al., "Anti-Bacterial Activity of *Euphorbia fusiformis*—A Rare Medicinal Herb", *Journal of Ethnopharmacology* 102:123-126 (2005).

Guarrera P.M., "Traditional Phytotherapy in Central Italy (Marche, Abruzzo, and Latium)", *Fitoterapia* 76(1):1-25 (2005).

Ogbourne S.M. et al., "Antitumor Activity of 3-Ingenyl Angelate: Plasma Membrane and Mitochondrial Disruption and Necrotic Cell Death", *Cancer Research* 64:2833-2839 (2004), XP-002998050.

Gillespie S.K. et al., "Ingenol 3-Angelate Induces Dual Modes of Cell Death and Differentially Regulates Tumor Necrosis Factor-Related Apoptosis-Inducing Ligand-Induced Apoptosis in Melanoma Cells", *Molecular Cancer Therapeutics* 3(12):1651-1658 (2004), XP-002447586.

Biswas T.K. et al., "Plant Medicines of Indian Origin for Wound Healing Activity: A Review", *Lower Extremity Wounds* 2(1):25-39 (2003).

Betancur-Galvis LA et al., "Cytotoxic and Antiviral Activities of Colombian Medicinal Plant Extracts of the *Euphorbia* Genus", *Mem Inst Oswaldo Cruz, Rio de Janeiro* 97(4):541-546 (2002).

El-Mekkaway S. et al., "Anti-HIV-1 Phorbol Esters from the Seeds of *Croton tiglium*", *Phytochemistry* 53:457-464 (2000).

Hohmann J. et al., "Diterpenoids from *Euphorbia peplus*", *Planta Med* 66:291-294 (2000).

Hohmann J. et al., "Jatrophane Diterpenoids from *Euphorbia peplus*", *Phytochemistry* 51:673-677 (1999).

Zayed S.M.A.D. et al., "Dietary Cancer Risk Conditional Cancerogens in Produce of Livestock Fed on Species of Spurge (*Euphorbiaceae*)-I. Skin Irritant and Tumor-Promoting Ingenane-Type Diterpene Esters in *E. pepulus*, One of Several Herbaceous *Euphorbia* Species Contaminating Fodder of Livestock", *J Cancer Res Clin Oncol* 124:131-140 (1998).

Zayed S.M.A.D. et al., "Dietary Cancer Risk from Conditional Cancerogens in Produce of Livestock Fed on Species of Spurge (*Euphorbiaceae*) III. Milk of Lactating Goats Fed on the Skin Irritant Herb *Euphorbia peplus* is Polluted by Tumor Promoters of the Ingenane Diterpene Ester Type", *Cancer Res Clin Oncol* 124:301-306 (1998).

Gura T., "Cancer Models: Systems for Identifying New Drugs Are Often Faulty", *Science* 278(5340):1041-1042 (pp. 1-6) (1997).

Hartwell L.H. et al., "Integrating Genetic Approaches into the Discovery of Anticancer Drugs", *Science* 278:1064-1068 (1997).

Krauter G. et al., "Structure/Activity Relationships of Polyfunctional Diterpenes of the Tigliane Type: A Pharmacophore Model for Protein-Kinase-C Activators Based on Structure/Activity Studie and Molecular Modeling of the Tumor Promoters 12-O-Tetradecanoylphorbol 13-Acetate and 3-O-Tetradecanoylingenol", *Eur. J Biochem.* 242:417-427 (1996).

Extract from Endocrinology *Proceedings of the American Association for Cancer Research* 36:256 (1995).

Dermer G.B., "Another Anniversary for the War on Cancer", *Bio/Technology* 12:320 (1994).

Jain R.K., "Barriers to Drug Delivery in Solid Tumors-Many", *Scientific American* 58-65 (1994).

Curti B.D., "Physical Barriers to Drug Delivery in Tumors", *Critical Reviews in Oncology/Hematology* 14:29-39 (1993).

Derwent Abstract Accession No. 1992-206104/32, DE 4102054 A dated Jul. 30, 1992.

Wu T-S et al., "Antitumor Agents, 119 Kansuiphorins A and B, Two Novel Antileukemic Diterpene Esters from *Euphorbia Kansui*", *Journal of Natural Products* 54(3):823-829 (1991).

Chowdhury E.H. et al., "The Phorbol Ester TPA Strongly Inhibits HIV-1-Induced Syncytia Formation but Enhances Virus Production: Possible Involvement of Protein Kinase C Pathway", *Virology* 176:126-132 (1990).

Laurence J. et al., "Phorbol Ester-Mediated Induction of HIV-1 From a Chronically Infected Promonocyte Clone: Blockade by Protein Kinase Inhibitors and Relationship to Tat-Directed Trans-Activation", *Biochemical and Biophysical Research Communications* 166(1):349-357 (1990).

Hamamoto Y. et al., "Comparison of Effects of Protein Kinase C Inhibitors on Phorbol Ester-Induced $CD_4$ Down-Regulation and Augmentation of Human Immunodeficiency Virus Replication in Human T Cell Lines", *Biochemical and Biophysical Research Communications* 164(1):339-344 (1989).

Benjamini E. et al., "Immunology-A Short Course", Chapter 2, Alan R. Liss, Inc., New York, pp. 15-18 (1988).

Abo K.A., "Irritancy of Ingenol Esters from *Euphorbia kamerunica*", *Fitoterapia* LIX(3):244-246 (1988).

Aitken A., "The Activation of Protein Kinase C by Daphnane, Ingenane and Tigliane Diterpenoid Esters", *Botanical Journal of the Linnean Society* 94:247-263 (1987).

Inoue S. et al., "Ingenane Synthetic Studies. Stereocontrolled Introduction of All Oxygenated and Unsaturated Centers in an Ingenol Prototype", *J. Org. Chem.* 52:5497-5498 (1987).

Schmidt R.J., "The Ingenane Polyol Esters", *Naturally Occurring Phorbol Esters*, pp. 245-269 (1986).

Nishizuka Y., "The Role of Protein Kinase C in Cell Surface Signal Transduction and Tumour Promotion", *Nature* 308:693-698 (1984).

Evans F.J. et al., "Pro-Inflammatory, Tumour-Promoting and Anti-Tumour Diterpenes of the Plant Families Euphorbiaceae and Thymelaeaceae", *Department of Pharmacognosy, The School of Pharmacy, University of London*, 44:90-99 (1983).

Freshney R.I., "Culture of Animal Cells-a Manual Basic Technique", *Department of Clinical Oncology Cancer Research Campaign Laboratories, University of Glasgow*—Alan R. Liss, Inc., 4 pages (1983).

Seip E.H. et al., "Skin Irritant Ingenol Esters from *Euphorbia esula*", *Planta Medica* 46:215-218 (1982).

El-Merzabani M.M. et al., "Screening System for Egyptian Plants With Potential Anti-Tumour Activity", *Planta Medica* 36:150-155 (1979).

Evans F.J. et al., "The Tigliane, Daphnane and Ingenane Diterpenes, Their Chemistry, Distribution and Biological Activities, A Review", *Lloydia* 41(3):193-233 (1978).

Hecker E., "Structure-Activity Relationships in Diterpene Esters Irritant and Cocarcinogenic to Mouse Skin", *Carcinogenesis* 2:11-48 (1978).

Weedon D. et al., "Home Treatment of Basal Cell Carcinoma", *The Medical Journal of Australia* 1:928 (1976).

Kupchan S.M. et al., "Gnidimacrin and Gnidimacrin 20-Palmitate Novel Macrocyclic Antileukemic Diterpenoid Esters from *Gnidia subcordata*" 5719-5720 (1976).

Kupchan S.M. et al., "Antileukemic Principles Isolated from Euphorbiaceae Plants", *Science* 191:571-572 (1975).

Uemura D. et al., "New Diterpene, 13-Oxyingenol, Derivative Isolated from *Euphorbia kansui* Liou", *Tetrahdron Letters* 29:2529-2532 (1974).

Kaminsky A. et al., "*Euforbia* Y Cantaridina En El Tratamiento Topico De Las Verrugas", *El Dia Medico* 51(31):1373-1382 (1959), together with a full English-language text translation except for the texts indicated as illegible on pp. 5, 6 and 7 of the translation.

Belkin M. et al., "Tumor-Damaging Capacity of Plant Materials. I. Plants Used as Cathartics", *Journal of the National Cancer Institute* 13:139-149 (1952).

Australian Search Report dated Jul. 23, 2008, corresponding to International Application No. PCT/AU2008/000596.

Australian Search Report dated Jan. 23, 2007, corresponding to International Application No. PCT/AU2006/001781.

European Search Report dated Sep. 4, 2007, corresponding to International Application No. PCT/GB2006/004739.

European Written Opinion of the International Searching Authority, corresponding to International Application No. PCT/GB2006/004739, Jun. 16, 2008.

Communication Pursuant to Article 94(3) EPC dated Jun. 23, 2009, in relation to European Patent Application No. 06820561.6.

Written Opinion corresponding to Singapore Patent Application No. 200804464-6, Aug. 6, 2009.

Hampson, P. et al., "PEP-005" *Drugs of the Future* (2005) pp. 1003-1005, vol. 30(10).

Ghorbani, A. "Studies on Pharmaceutical Ethnobotnay in the Region of Turkmen Sahra, North of Iran (Part I): General Results" *Journal of Ethnopharmacology* (2005) pp. 58-68, vol. 102(1).

Rasik, A.M. et al., "Wound Healing Activity of Latex of *Euphorbia neriifolia* Linn" *Indian Journal of Pharmacology* (1996) pp. 107-109, vol. 28(2).

Supplementary European Search Report dated Jan. 15, 2010.

Cheever, M. A. et al., "Potential Uses of Interleukin 2 in Cancer Therapy" *Immunobiology* (1986) pp. 365-382, vol. 172.

Timmerman, J. M. et al., "Dendritic Cell Vaccines for Cancer Immunothereapy" *Annual Review of Medicine* (1999) pp. 507-529, vol. 50.

Shimizu, K. et al., "Potentiation of Immunologic Responsiveness to Dendritic Cell-Based Tumor Vaccines by Recombinant Interleukin-2" *The Cancer Journal* (2000) pp. S67-S75, vol. 6(Supplement 1).

Challacombe, J. M. et al., "Neutrophils Are a Key Component of the Antitumor Efficacy of Topical Chemotherapy with Ingenol-3-Angelate" *The Journal of Immunology* (2006) pp. 8123-8132, vol. 177(11).

Le, T. et al., "Immunostimulatory Cancer Chemotherapy Using Local Ingenol-3-Angelate and Synergy with Immunotherapies" *Vaccine* (2009) pp. 3053-3062, vol. 27(23).

Supplementary European Search Report dated Jun. 4, 2010.

Third Party Observations filed in related European Patent Application No. EP 01940015.9, dated May 23, 2011, including copies of the prior art from India's Traditional Knowledge Digital Library discussed in the Observations and English translation thereof.

Third Party Observations filed in related Canadian Patent Application No. CA 2,411,726, dated Mar. 2, 2011, including copies of the prior art from India's Traditional Knowledge Digital Library discussed in the Observations and English translation thereof.

Samuelsson, G. et al., "Inventory of Plants used in Traditional Medicin in Somalia. II. Plants of the Families Combretaceae to Labiatae" *Journal of Ethnopharmacology* (1992) pp. 47-70, vol. 37.

Third Party Observations filed in related Canadian Patent Application No. CA 2,411,596, dated Jul. 11, 2011, including copies of the prior art as found in Traditional Knowledge Digital Library discussed in the Observations and English translation thereof.

Third Party Observations filed in related European Patent Application No. EP 01937873.6, dated May 25, 2011, including copies of the prior art as found in Traditional Knowledge Digital Library discussed in the Observations and English translation thereof.

Nickel, A. et al., "Total Synthesis of Ingenol" Journal of the American Chemical Society (2004) pp. 16300-16301, vol. 126, No. 50.

* cited by examiner

TREATMENT OF SOLID CANCERS

BACKGROUND OF THE INVENTION

1. Field of the Invention

The present invention relates generally to the field of cancer including tumor therapy. More particularly, the present invention relates to the treatment of solid cancers, including solid tumors, and the prevention or reduction of cancer metastasis, by chemoablation of cancer cells by an agent which also stimulates the generation of cancer-specific T-cells, a process referred to herein as immunostimulatory chemoablation. The present invention further contemplates combination therapy comprising immunostimulatory chemoablation and one or more other therapeutic regimens, which enhance, co-operate and/or synergize with the cancer-specific T-cells induced by the chemoablation. The present invention also relates to pharmaceutical compositions for use in treating cancers.

2. Description of the Prior Art

Bibliographic details of references provided in the subject specification are listed at the end of the specification.

Reference to any prior art in this specification is not, and should not be taken as, an acknowledgment or any form of suggestion that this prior art forms part of the common general knowledge in any country.

Although chemotherapy has been useful to prolong survival, to increase tissue conserving surgery, and to increase remission rates for several cancer types, the high mortality of cancers such as breast, lung and colorectal carcinomas, which account for the majority of cancer deaths, have remained problematic during the past 25 years from the standpoint of achieving significant advances in outcomes. This is true despite major changes in surgical and radiation protocols including combinatorial drug and drug-radiation regimens and new approaches to the staging of treatments. This relatively modest improvement is reflected in National Cancer Institute data as presented in the Surveillance, Epidemiology and End Results (SEER) 1973-1997 Cancer Statistics Review (NCI-NIH 2000).

From these data, it appears that there has been little change in the ratio of incidence (diagnosis) to mortality rate in the short term period 1997-2000 for breast cancer (180200 diagnosed/41945 deaths in 1997 vs 182800/40800 in 2000), for lung cancer (178100/153200 in 1997 vs 164100/156900 in 2000) and for colorectal cancer (131200/56695 in 1997 vs 130200/56300 in 2000). Some changes do seem to be attributable to various evolving "conventional" treatments over the long term when one compares 1950 with 1997 data. However, there have been so many therapeutic, diagnostic and demographic changes during this extended time period that it is extremely difficult to clearly attribute improvements in outcomes to specific "standard of care" regimens. For example, based on the SEER report, the ratio of the annual % change for diagnosis to the annual % change of the mortality rate during the period 1950-1997 is: breast (+1.3%/0.1%), lung (+2.3%/+2.9%) and colorectal (0.1%/0.9%). Using estimates for the past 20 years, increasing diagnosis for breast (+29%) and lung (+58%) has been observed but only a 2% decline in breast cancer mortality and a disturbing 77% increase in lung cancer mortality during this time. Even with the remarkable advances in health care during the past 50 years there appear to be only modest and interpretatively complicated changes for outcomes in the treatment of high mortality cancers; except for lung cancer where the diagnosis and especially the mortality have been clearly on the rise.

In work leading to the present invention, the subject inventors recognized that one limitation of current chemotherapeutic agents is its toxicity to the immune system. Thus, combining chemotherapy with immune-based therapies, which intend to induce anti-cancer T-cell activity, is often compromised by the immunosuppressive effect of the chemotherapy, which generally suppress formation of cancer-specific T-cells. Although some local chemotherapy can induce anti-cancer immunity, it is widely recognized that chemotherapeutic treatments result in suboptimal induction of functional anti-cancer T-cells.

Accordingly, there is a clear need for more effective therapeutic treatments for solid cancers which include solid tumors. The present invention provides a method of treating a range of solid cancers in a subject using, inter alia, an agent which may be applied directly or proximally to the cancer and which operates via a mode of action which induces immunostimulatory chemoablation of the cancer cells. In particular, the chemoablation agent stimulates the generation of T-cells and more particularly $CD8^+$ T-cells and $CD4^+$ T-cells having cancer cell specificity and further that this immunostimulatory chemoablatory can enhance, co-operate and/or synergize with other immune-based therapeutic regimens to enhance anti-cancer therapy.

SUMMARY OF THE INVENTION

Throughout this specification, unless the context requires otherwise, the word "comprise", or variations such as "comprises" or "comprising", will be understood to imply the inclusion of a stated element or integer or group of elements or integers but not the exclusion of any other element or integer or group of elements or integers.

Nucleotide and amino acid sequences are referred to by a sequence identifier number (SEQ ID NO:). The SEQ ID NOs: correspond numerically to the sequence identifiers <400>1 (SEQ ID NO:1), <400>2 (SEQ ID NO:2), etc. A summary of the sequence identifiers is provided in Table 2. A sequence listing is provided after the claims.

In one aspect, the present invention contemplates a method for treating or preventing cancer growth and/or metastasis in a subject, said method comprising administering directly or proximally to said cancer, one or more angeloyl substituted ingenanes or derivatives thereof in an amount effective to induce primary necrosis in at least the cancer cells and to stimulate the generation of cancer-specific T-cells. The cancer-specific T-cells include $CD8^+$ T-cells and $CD4^+$ T-cells or precursors thereof or a subset thereof. The present invention further contemplates the use of angeloyl substituted ingenanes or derivatives thereof in combination with genetic, immunological or cytological agents which enhance, co-operate or otherwise synergize the induced cancer-specific T-cells or with other anti-cancer regimens including radiotherapy and chemotherapy in the treatment of cancer. The method of the present invention assists in the treatment of primary tumors and/or prevents or reduces the growth of secondary tumors, i.e. metastases. Thus, this immunostimulatory chemoablation therapy not only debulks the tumor burden but in so doing also induces cancer-specific T-cells such as $CD8^+$ T-cells and $CD4^+$ T-cells.

The present invention further contemplates a method for treating a secondary cancer in a subject, said method comprising administering an angeloyl substituted ingenane or a derivative thereof directly or proximal to a primary cancer in an amount effective to induce primary necrosis in at least the cancer cells and to stimulate the generation of cancer-specific T-cells. The secondary cancer is a cancer distant to the primary cancer. As indicated above, the cancer-specific T-cells include CD8+ T-cells and CD4+ T-cells.

Reference herein to a "cancer" includes reference to a tumor. Accordingly, the present invention relates generally to cancer including tumor therapy.

The angeloyl substituted ingenanes (also referred to as an ingenol angelate) or derivatives thereof may be synthetically produced or may be derived from extracts of a plant of the Euphorbiaceae family. *Euphorbia peplus* is particularly useful as a source of ingenol angelates for use in the practice of the present invention. Preferred angeloyl substituted ingenanes or derivatives thereof, include but are not limited to, ingenol-3-angelate (PEP005), 20-deoxy-ingenol-3-angelate (PEP006), 20-O-acetyl-ingenol-3-angelate (PEP008), or derivatives thereof, or pharmaceutically acceptable salts of these. In a most preferred embodiment, the ingenol angelate is ingenol-3-angelate and is referred to herein as "PEP005". A derivative includes components which are no longer angeloyl substituted ingenanes. Reference herein to "PEP005" or its chemical name "ingenol-3-angelate" includes derivatives thereof as well as naturally occurring or synthetic forms.

As used herein, the term "administering directly or proximally to said cancer" should be understood to include administration of the angeloyl substituted ingenanes or derivatives thereof to the cancer per se and/or to the local region of the cancer in the subject. This includes, inter alia, topical, intra-tumoral (i.t.) or intra-lesional (i.l.) and/or peri-tumoral (p.t.) administration of the agent wherein the agent is directly injected or otherwise introduced into the cancer itself and/or the area of cancer growth. Administration of the agent may also be via an artery which substantially feeds the cancer or a local region surrounding or proximal to the cancer such that a relatively high concentration of the agent is accumulated at the site of the cancer. Such administration includes, for example, administration of the agent to the hepatic artery for the treatment of hepatocellular carcinomas. Local administration of the angeloyl substituted ingenanes or derivatives thereof to the cancer is contemplated and this includes topical administration to an epithelial or endothelial surface, topical administration to the surface of a cancer which is exposed during surgery or topical administration to the gastrointestinal tract by ingestion.

The genetic, immunological or cytological therapy may be provided at a distant site to the cancer. The aim of the genetic, immunological or cytological therapy is to generate anti-cancer immunity which enhances, co-operates and/or synergizes with anti-cancer T-cells induced by immuno-potentiating chemoablation, i.e. immunostimulatory chemoablation. As indicated above, the preferred cancer T-cells are CD8+ T-cells and CD4+ T-cells and their homologs or precursors.

In one embodiment, the angeloyl substituted ingenanes or derivatives thereof are co-administered with an agent or treatment which enhances, co-operates or synergizes with the ingenol angelate-induced cancer-specific T-cells. Such agents include inter alia an interleukin molecule, such as but not limited to IL-2, IL-7 and IL-15, a cytokine such as GM-CSF, an antibody such as anti-CD40 antibody or anti-CTLA4 antibody, an agent which removes suppressor T-cells or any other agent which potentiates cancer-specific T-cells.

In another embodiment, the angeloyl substituted ingenanes or derivatives thereof are co-administered with a cancer vaccine such as a Dendritic Cell (DC) vaccine and/or a vaccine comprising a virus vector or recombinant protein or peptide or cancer cell lysate which is capable of presenting a cancer antigen or epitope to the immune system. Hence, the present invention contemplates combination therapies including the administration of an ingenol angelate and a cancer vaccine or other cancer-specific T-cell potentiating agent optionally together with radiation therapy or other anti-cancer therapies.

The present invention further contemplates a pharmaceutical composition comprising an angeloyl substituted ingenane or derivative thereof which is capable of causing primary necrosis of cancer cells and inducing the generation of cancer-specific T-cells or a subset thereof together with a pharmaceutically acceptable carrier and/or diluent. The composition itself or a pharmaceutical formulation comprising the pharmaceutical composition may also contain one or more genetic, immunological or cytological agents including agents which enhance co-operate and/or synergize with cancer-specific T-cells. An agent which enhances cancer-specific T-cells is also referred to herein as a cancer-specific T-cell potentiating agents.

A list of commonly used abbreviations used herein is provided in Table 1.

TABLE 1

Abbreviations

| Abbreviation | Description |
| --- | --- |
| Cancer-specific CD4+ T-cell | CD4+ lymphocyte with cancer cell specificity |
| Cancer-specific CD8+ T-cell | αβ CD8+ lymphocyte with cancer cell specificity |
| CpG ODN | CpG Oligodeoxynucleotide |
| d0 | Day zero |
| DC | Dendritic Cell |
| GM-CSF | Granulocyte-Macrophage Colony Stimulating Factor |
| i.l. | Intra-lesional |
| i.p. | Intra-peritoneal |
| i.t. | Intra-tumoral |
| i.v. | Intra-venous |
| IL-15 | Interleukin 15 |
| IL-2 | Interleukin-2 |
| IL-7 | Interleukin 7 |
| Local administration | Covers topical, i.i., i.t. and p.t. administration |
| OVA | Ovalbumin |
| PBMC | Peripheral Blood Mononuclear Cells |
| p.t. | peri-tumoral |
| PEP005 | Ingenol-3-angelate |
| PEP006 | 20-deoxy-ingenol-3-angelate |
| PEP008 | 20-O-acetyl-ingenol-3-angelate |
| s.c. | Subcutaneous |

A summary of the sequence identifiers used herein is shown in Table 2

TABLE 2

Sequence Identifiers

| Sequence Identifier | Sequence |
| --- | --- |
| SEQ ID NO: 1 | Dominant Trp2 CD8+ T-cell epitope for anti-B/6 CD8+ T-cells |
| SEQ ID NO: 2 | CD8+ T-cell epitope for ovalbumin |
| SEQ ID NO: 3 | Trp-2 epitope (human) |
| SEQ ID NO: 4 | human gp100 epitope |
| SEQ ID NO: 5 | Epitope on CT26 colon carcinoma cells |

DETAILED DESCRIPTION OF THE INVENTION

Figure 1:
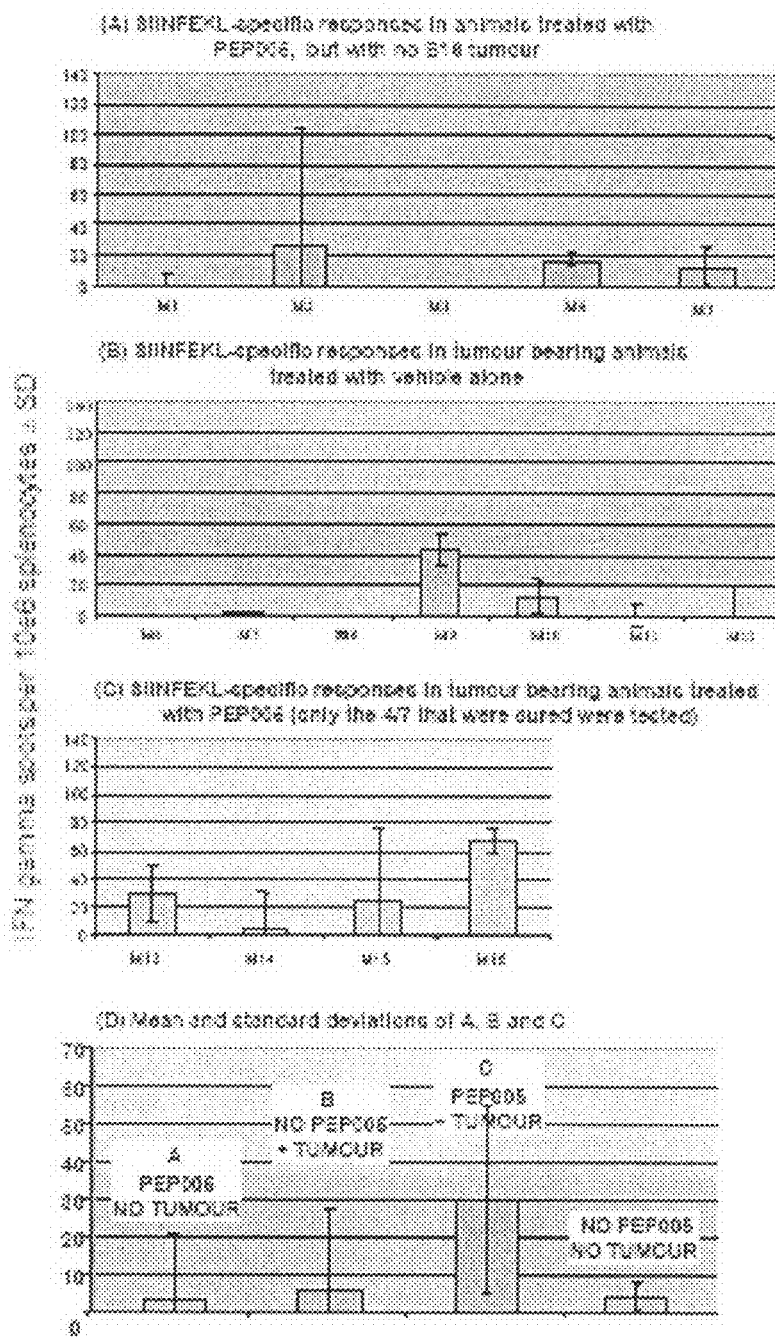
FIGS. 1A to 1D are graphical representations showing; (A) SIINFEKL [SEQ ID NO:3]-specific responses in animals treated with PEP005 but with no B16 tumor; (B) SIINFEKL [SEQ ID NO:3]-specific responses in tumor bearing animals treated with vehicle alone; (C) SIINFEKL [SEQ ID NO:3]-specific responses in tumor bearing animals treated with PEP005 (only the 4/7 that were cured were tested); and (D) Mean and SDs of (A), (B) and (C).

It is to be understood that unless otherwise indicated, the subject invention is not limited to specific formulations, manufacturing methods, therapeutic protocols, or the like as such may vary. It is also to be understood that the terminology used herein is for the purpose of describing particular embodiments only and is not intended to be limiting.

It must be noted that, as used in the subject specification, the singular forms "a", "an" and "the" include plural aspects unless the context already dictates otherwise. Thus, for example, reference to "a cancer" includes a single cancer as well as two or more cancers; "a T-cell" includes a T-cell as well as two or more T-cells; "an Interleukin" includes a single Interleukin molecule or two or more Interleukin molecules and so forth.

In one aspect, the present invention contemplates a method for treating or preventing cancer growth and/or metastasis in a subject, said method comprising administering directly or proximally to said cancer, one or more angeloyl substituted ingenanes or derivatives thereof in an amount effective to induce primary necrosis in at least the cancer cells and to stimulate the generation of cancer-specific T-cells.

In another aspect, the present invention further contemplates a method for treating a secondary cancer in a subject, said method comprising administering an angeloyl substituted ingenane or a derivative thereof directly to proximal to a primary cancer in an amount effective to induce primary necrosis in at least the cancer cells and to stimulate the generation of cancer-specific T-cells.

The present invention further contemplates the use of angeloyl substituted ingenanes or derivatives thereof in combination with genetic, immunological or cytological agents which enhance, co-operate or otherwise synergize the induced cancer-specific T-cells or with other anti-cancer regimens including radiotherapy and chemotherapy in the treatment of cancer.

Furthermore, the present invention contemplates the use of an angeloyl substituted ingenane in combination with an agent which enhances, co-operates or synergizes with cancer-specific T-cells in the generation of a therapeutic protocol for the treatment of cancer.

Reference herein to "cancer-specific T-cells" includes in a preferred embodiment cancer-specific CD8+ T-cells and their homologs and/or precursors. Reference to "CD8+ T-cells" includes subtypes of these cells. Cancer-specific CD4+ T-cells may also be induced as well as their homologs, precursors or subtypes. A subtype includes a subset. The terms "T-cell" and "T-lymphocyte" are used interchangeably through the specification and refers to the same cell.

The use of an angeloyl substituted ingenane to induce necrosis of cancer cells and an immune response is referred to herein as "immunostimulatory chemoabalation". The immune response includes both a T-cell response and optionally an antibody response (e.g. IgG).

Accordingly, the present invention provides a method for treating or preventing the growth and/or metastasis of solid cancers in a subject. As used herein, a "solid cancer" refers to one or more cells which are growing or have grown in an uncontrolled manner to form cancer tissue. As used herein, the term "solid cancer" includes, but is not limited to "carcinomas", "adenocarcinomas" and "sarcomas". "Sarcomas" are cancers of the connective tissue, cartilage, bone, muscle, and so on. "Carcinomas" are cancers of epithelial (lining) cells. "Adenocarcinoma" refers to carcinoma derived from cells of glandular origin. The terms "cancer" and "tumor" are used interchangeably throughout the subject specification.

Solid cancers may arise in nearly any tissue of the body and the treatment of any solid cancer is contemplated by the present invention. Exemplary "solid cancers" which may be treated in accordance with the present invention include AIDS related cancer, acoustic neoma, adenocystic carcinoma, adrenocortical cancer, agnogenic myeloid metaplasia, alopecia, alveolar soft-part sarcoma, anal cancer, angiosarcoma, aplastic anaemia, astrocytoma, ataxia-telangiectasia, basal cell carcinoma (bcc), bladder cancer, bone cancers, bowel cancer, brain stem glioma, brain and CNS cancers, breast cancer, CNS cancers, carcinoid cancers, cervical cancer, childhood brain cancers, childhood cancer, childhood soft tissue sarcoma, chondrosarcoma, choriocarcinoma, colorectal cancers, cutaneous T-Cell lymphoma, dermatofibrosarcoma-protuberans, desmoplastic small round cell cancer, ductal carcinoma, endocrine cancers, endometrial cancer, ependymoma, esophageal cancer, Ewing's sarcoma, extra hepatic bile duct cancer, eye cancer, eye: melanoma, retinoblastoma, fallopian tube cancer, fanconi anaemia, fibrosarcoma, gall bladder cancer, gastric cancer, gastrointestinal cancers, gastrointestinal carcinoid cancer, genitourinary cancers, germ cell cancers, gestational trophoblastic disease, glioma, gynecological cancers, hematological malignancies, head and neck cancer, hepatocellular cancer, hereditary breast cancer, histiocytosis, Hodgkin's disease, human papillomavirus, hydatidiform mole, hypercalcemia, hypopharynx cancer, intra-ocular melanoma, isle T-cell cancer, Kaposi's sarcoma, kidney cancer, Langerhan's cell histiocytosis, laryngeal cancer, leiomyosarcoma, li-fraumeni syndrome, lip cancer, liposarcoma, liver cancer, lung cancer, lymphedema, lymphoma, Hodgkin's lymphoma, non-Hodgkin's lymphoma, male breast cancer, malignant rhabdoid cancer of kidney, medulloblastoma, melanoma, merkel cell cancer, mesothelioma, metastatic cancer, mouth cancer, multiple endocrine neoplasia, mycosis fungoides, myelodysplastic syndromes, myeloma, myeloproliferative disorders, nasal cancer, nasopharyngeal cancer, nephroblastoma, neuroblastoma, neurofibromatosis, nijmegen breakage syndrome, non-melanoma skin cancer, non-small cell lung cancer (nsclc), ocular cancers, oesophageal cancer, oral cavity cancer, oropharynx cancer, osteosarcoma, ostomy ovarian cancer, pancreas cancer, paranasal cancer, parathyroid cancer, parotid gland cancer, penile cancer, peripheral neuroectodermal cancers, pituitary cancer, polycythemia vera, prostate cancer, rare cancers and associated disorders, renal cell carcinoma, retinoblastoma, rhabdomyosarcoma, rothmund Thomson syndrome, salivary gland cancer, sarcoma, schwannoma, sezary syndrome, skin cancer, small cell lung cancer (scic), small intestine cancer, soft tissue sarcoma, spinal cord cancers, squamous cell carcinoma (scc), stomach cancer, synovial sarcoma, testicular cancer, thymus cancer, thyroid cancer, transitional cell cancer (bladder), transitional cell cancer (renal-pelvis-/-ureter), trophoblastic cancer, urethral cancer, urinary system cancer, uroplakins, uterine sarcoma, uterus cancer, vaginal Cancer, vulva cancer, Waldenstrom's macroglobulinemia and Wilms' Cancer.

The solid cancer which is treated using the methods of the present invention may be a primary lesion or may be the result of metastasis of a primary cancer. Furthermore, if the solid cancer is a metastasis of a primary cancer, the primary cancer may be either a primary solid cancer as described above or may be a dispersed primary cancer such as a leukemia or lymphoma.

The angeloyl substituted ingenanes or derivatives thereof contemplated herein effect primary necrosis in one or more eukaryotic cell types. Importantly, the angeloyl substituted ingenanes or derivatives thereof induce chemoablation of the cancer tissue and stimulate the immune system to generate cancer-specific T-cells such as $CD8^+$ T-cells and $CD4^+$ T-cells. An antibody response such as IgG may also be induced.

The angeloyl substituted ingenanes or derivatives thereof are conveniently derived from extracts of a plant of the Euphorbiaceae family, although the present invention contemplates an angeloyl substituted ingenane or derivatives thereof prepared by chemical synthesis or chemical modification of a plant-derived molecule. The effect of modification may be to generate a compound which is not strictly an angeloyl substituted ingenane. Such derivatives are still within the scope of the present invention.

Reference herein to "a plant of the Euphorbiaceae family" includes plants from the genera *Acalypha, Acidoton, Actinostemon, Adelia, Adenocline, Adenocrepis, Adenophaedra, Adisca, Agrostistachys, Akhornea, Alchorneopsis, Alcinaeanthus, Alcoceria, Aleurites, Amanoa, Andrachne, Angostyles, Anisophyllum, Antidesma, Aphora, Aporosa, Aporosella, Argythamnia, Astrococcus, Astrogyne, Baccanrea, Baliospermum, Bernardia, Beyeriopsis, Bischofia, Blachia, Blumeodondron, Bonania, Bradleia, Breynia, Breyniopsis, Briedelia, Buraeavia, Caperonia, Caryodendron, Celianella, Cephalocroton, Chaenotheca, Chaetocarpus, Chamaesyce, Cheilosa, Chiropetalum, Choriophyllum, Cicca, Chaoxylon, Cleidon, Cleistanthus, Cluytia, Cnesmone, Cnidoscolus, Coccoceras, Codiaeum, Coelodiscus, Conami, Conceveiba, Conceveibastrum, Conceveïbum, Corythea, Croizatia, Croton, Crotonopsis, Crozophora, Cubanthus, Cunuria, Dactylostemon, Dalechampia, Dendrocousinsia, Diaspersus, Didymocistus, Dimorphocalyx, Discocarpus, Ditaxis, Dodecastingma, Drypetes, Dysopsis, Elateriospermum, Endadenium, Endospermum, Erismanthus, Erythrocarpus, Erythrochilus, Eumecanthus, Euphorbia, Euphorbiodendron, Excoecaria, Flueggea, Calearia, Garcia, Gavarretia, Gelonium, Giara, Givotia, Glochidion, Clochidionopsis, Glycydendron, Gymnanthes, Gymnosparia, Hematospermum, Hendecandra, Hevea, Hieronima, Hieronyma, Hippocrepandra, Homalanthus, Hymenocardia, Janipha, Jatropha, Julocroton, Lasiocroton, Leiocarpus, Leonardia, Lepidanthus, Leucocroton, Mabea, Macaranga, Mallotus, Manihot, Mappa, Maprounea, Melanthesa, Mercurialis, Mettenia, Micrandra, Microdesmis, Microelus, Microstachy, Maocroton, Monadenium, Mozinna, Neoscortechinia, Omalanthus, Omphalea, Ophellantha, Orbicularia, Ostodes, Oxydectes, Palenga, Pantadenia, Paradrypeptes, Pausandra, Pedilanthus, Pera, Peridium, Petalostigma, Phyllanthus, Picrodendro, Pierardia, Pilinophytum, Pimeleodendron, Piranhea, Platygyna, Plukenetia, Podocalyx, Poinsettia, Poraresia, Prosartema, Pseudanthus, Pycnocoma, Quadrasia, Reverchonia, Richeria, Richeriella, Ricinella, Ricinocarpus, Rottlera, Sagotia, Samwithia, Sapium, Savia, Sclerocroton, Sebastiana, Securinega, Senefeldera, Senefilderopsis, Serophyton, Siphonia, Spathiostemon, Spixia, Stillingia, Strophioblachia, Synadenium, Tetracoccus, Tetraplandra, Tetrorchidium, Thyrsanthera, Tithymalus, Trageia, Trewia, Trigonostemon, Tyria* and *Xylophylla*.

The most preferred genus and most suitable for the practice of the present invention is the genus *Euphorbia*. Particularly useful species of this genus include *Euphorbia aaron-rossii, Euphorbia abbreviata, Euphorbia aceta, Euphorbia alatocaulis, Euphorbia albicaulis, Euphorbia algomarginata, Euphorbia aliceae, Euphorbia alta, Euphorbia anacampseros, Euphorbia andromedae, Euphorbia angusta, Euphorbia anthonyi, Euphorbia antiguensis, Euphorbia apocynifolia, Euphorbia arabica, Euphorbia ariensis, Euphorbia arizonica, Euphorbia arkansana, Euphorbia arteagae, Euphorbia arundelana, Euphorbia astroites, Euphorbia atrococca, Euphorbia baselicis, Euphorbia batabanensis, Euphorbia bergeri, Euphorbia bermudiana, Euphorbia bicolor, Euphorbia biformis, Euphorbia bifurcata, Euphorbia bilobata, Euphorbia biramensis, Euphorbia biuncialis, Euphorbia blepharostipula, Euphorbia blodgetti, Euphorbia boerhaavioides, Euphorbia boliviana, Euphorbia bracei, Euphorbia brachiata, Euphorbia brachycera, Euphorbia brandegee, Euphorbia brittonii, Euphorbia caesia, Euphorbia calcicola, Euphorbia campestris, Euphorbia candelabrum, Euphorbia capitellata, Euphorbia carmenensis, Euphorbia carunculata, Euphorbia cayensis, Euphorbia celastroides, Euphorbia chalicophila, Euphorbia chamaerrhodos, Euphorbia chamaesula, Euphorbia chiapensis, Euphorbia chiogenoides, Euphorbia cinerascens, Euphorbia clarionensis, Euphorbia colimae, Euphorbia colorata, Euphorbia commutata, Euphorbia consoquitlae, Euphorbia convolvuloides, Euphorbia corallifera, Euphorbia creberrima, Euphorbia crenulata, Euphorbia cubensis, Euphorbia cuspidata, Euphorbia cymbiformis, Euphorbia darlingtonii, Euphorbia defoliata, Euphorbia degeneri, Euphorbia deltoidea, Euphorbia dentata, Euphorbia depressa Euphorbia dictyosperma, Euphorbia dictyosperma, Euphorbia dioeca, Euphorbia discoidalis, Euphorbia dorsiventralis, Euphorbia drumondii, Euphorbia duclouxii, Euphorbia dussii, Euphorbia eanophylla, Euphorbia eggersii, Euphorbia eglandulosa, Euphorbia elata, Euphorbia enalla, Euphorbia eriogonoides, Euphorbia eriophylla, Euphorbia esculaeformis, Euphorbia espirituensis, Euphorbia esula, Euphorbia excisa, Euphorbia exclusa, Euphorbia exstipitata, Euphorbia exstipulata, Euphorbia fendleri, Euphorbia filicaulis, Euphorbia filiformis, Euphorbia florida, Euphorbia fruticulosa, Euphorbia garber, Euphorbia gaumerii, Euphorbia gerardiana, Euphorbia geyeri, Euphorbia glyptosperma, Euphorbia gorgonis, Euphorbia gracilior, Euphorbia gracillima, Euphorbia gradyi, Euphorbia graminea, Euphorbia graminiea Euphorbia grisea, Euphorbia guadalajarana, Euphorbia guanarensis, Euphorbia gymnadenia, Euphorbia hematantha, Euphorbia hedyotoides, Euphorbia heldrichii, Euphorbia helenae, Euphorbia helleri, Euphorbia helwigii, Euphorbia henricksonii, Euphorbia heterophylla, Euphorbia hexagona, Euphorbia hexagonoides, Euphorbia hinkleyorum, Euphorbia hintonii, Euphorbia hirtula, Euphorbia hirta, Euphorbia hooveri, Euphorbia humistrata, Euphorbia hypericifolia, Euphorbia inundata, Euphorbia involuta, Euphorbia jaliscensis, Euphorbia jejuna, Euphorbia johnston, Euphorbia juttae, Euphorbia knuthii, Euphorbia lasiocarpa, Euphorbia lata, Euphorbia latazi, Euphorbia lat-* ericolor, Euphorbia laxiflora Euphorbia lecheoides, Euphorbia ledienii, Euphorbia leucophylla, Euphorbia lineata, Euphorbia linguiformis, Euphorbia longecornuta, Euphorbia longepetiolata, Euphorbia longeramosa, Euphorbia longinsulicola, Euphorbia longipila, Euphorbia lupulina, Euphorbia lurida, Euphorbia lycioides, Euphorbia macropodoides, macvaughiana, Euphorbia manca, Euphorbia mandoniana, Euphorbia mangleti, Euphorbia mango, Euphorbia marylandica, Euphorbia mayana, Euphorbia melanadenia, Euphorbia melanocarpa, Euphorbia meridensis, Euphorbia mertonii, Euphorbia mexiae, Euphorbia microcephala, Euphorbia microclada, Euphorbia micromera, Euphorbia misella, Euphorbia missurica, Euphorbia montana, Euphorbia montereyana, Euphorbia multicaulis, Euphorbia multiformis, Euphorbia multinodis, Euphorbia multiseta, Euphorbia muscicola, Euphorbia neomexicana, Euphorbia nephradenia, Euphorbia niqueroana, Euphorbia oaxacana, Euphorbia occidentalis, Euphorbia odontodenia, Euphorbia olivacea, Euphorbia olowaluana, Euphorbia opthalmica, Euphorbia ovata, Euphorbia pachypoda, Euphorbia pachyrhiza, Euphorbia padifolia, Euphorbia palmeri, Euphorbia paludicola, Euphorbia parciflora, Euphorbia parishii, Euphorbia parryi, Euphorbia paxiana, Euphorbia pediculifera, Euphorbia peplidion, Euphorbia peploides, Euphorbia peplus, Euphorbia pergamena, Euphorbia perlignea, Euphorbia petaloidea, Euphorbia petaloidea, Euphorbia petrina, Euphorbia picachensis, Euphorbia pilosula, Euphorbia pilulifera, Euphorbia pinariona, Euphorbia pinetorum, Euphorbia pionosperma, Euphorbia platysperma, Euphorbia plicata, Euphorbia poeppigii, Euphorbia poliosperma, Euphorbia polycarpa, Euphorbia polycnemoides, Euphorbia polyphylla, Euphorbia portoricensis, Euphorbia portulacoides Euphorbia portulana, Euphorbia preslii, Euphorbia prostrata, Euphorbia pteroneura, Euphorbia pycnanthema, Euphorbia ramosa, Euphorbia rapulum, Euphorbia remyi, Euphorbia retroscabra, Euphorbia revoluta, Euphorbia rivularis, Euphorbia robusta, Euphorbia romosa, Euphorbia rubida, Euphorbia rubrosperma, Euphorbia rupicola, Euphorbia sanmartensis, Euphorbia saxatilis M. Bieb, Euphorbia schizoloba, Euphorbia sclerocyathium, Euphorbia scopulorum, Euphorbia senilis, Euphorbia serpyllifolia, Euphorbia serrula, Euphorbia setiloba Engelm, Euphorbia sonorae, Euphorbia soobyi, Euphorbia sparsiflora, Euphorbia sphaerosperma, Euphorbia syphilitica, Euphorbia spruceana, Euphorbia subcoerulea, Euphorbia stellata, Euphorbia submammilaris, Euphorbia subpeltata, Euphorbia subpubens, Euphorbia subreniforme, Euphorbia subtrifoliata, Euphorbia succedanea, Euphorbia tamaulipasana, Euphorbia telephioides, Euphorbia tenuissima, Euphorbia tetrapora, Euphorbia tirucalli, Euphorbia tomentella, Euphorbia tomentosa, Euphorbia torralbasii, Euphorbia tovariensis, Euphorbia trachysperma, Euphorbia tricolor, Euphorbia troyana, Euphorbia tuerckheimii, Euphorbia turczaminowii, Euphorbia umbellulata, Euphorbia undulata, Euphorbia vermiformis, Euphorbia versicolor, Euphorbia villifera, Euphorbia violacea, Euphorbia whitei, Euphorbia xanti Engelm, Euphorbia xylopoda Greenm., Euphorbia yayalesia Urb., Euphorbia yungasensis, Euphorbia zerayschanica and Euphorbia zinniiflora.

Particularly preferred species of the genus Synadenium include Synadenium grantii and Synadenium compactum.

Particularly preferred species of the genus Monadenium include Monadenium lugardae and Monadenium guentheri.

A preferred species of the genus Endadenium is Endadenium gossweileni.

Euphorbia peplus is a particularly useful plant from which to isolate the angeloyl substituted ingenanes or derivatives thereof used in the practice of the present invention. Reference herein to "Euphorbia peplus" or its abbreviation "E. peplus" includes various varieties, strains, lines, hybrids or derivatives of this plant as well as its botanical or horticultural relatives. Furthermore, the present invention may be practiced using a whole Euphorbiaceae plant or parts thereof including sap or seeds or other reproductive material may be used. Generally, for seeds or reproductive material to be used, a plant or plantlet is first required to be propagated.

Reference herein to a plant of the Euphorbiaceae family, a Euphorbia species or E. peplus further encompasses genetically modified plants. Genetically modified plants include transgenic plants or plants in which a trait has been removed or where an endogenous gene sequence has been down-regulated, mutated or otherwise altered including the alteration or introduction of genetic material which exhibits a regulatory effect on a particular gene. Consequently, a plant which exhibits a character not naturally present in a plant of the Euphorbiaceae family or a species of Euphorbia or in E. peplus is nevertheless encompassed by the present invention and is included within the scope of the above-mentioned terms.

The angeloyl substituted ingenanes or derivatives thereof are generally found in extracts of plants of the Euphorbiaceae family. An extract may comprise, therefore, sap or liquid or semi-liquid material exuded from, or present in, leaves, stem, flowers, seeds, bark or between the bark and the stem. Most preferably, the extract is from sap. Furthermore, the extract may comprise liquid or semi-liquid material located in fractions extracted from sap, leaves, stems, flowers, bark or other plant material of the Euphorbiaceace plant. For example, plant material may be subject to physical manipulation to disrupt plant fibres and extracellular matrix material and inter- and intra-tissue extracted into a solvent including an aqueous environment. All such sources of the angeloyl substituted ingenanes or derivatives thereof are encompassed by the present invention including angeloyl substituted ingenanes or derivatives thereof obtained by synthetic routes.

The angeloyl substituted ingenanes or derivatives thereof of the present invention may be in purified or isolated form meaning that the preparation is substantially devoid of other compounds or contaminating agents other than a diluent, solvent, gel, paste or carrier or isoforms of the agents. Furthermore, the term "angeloyl substituted ingenanes or derivatives thereof" includes preparations of two or more compounds either admixed together or co-purified from a particular source. The angeloyl substituted ingenanes or derivatives thereof may also be comprised within a chemical fraction, extract or other preparation from the plant of the Euphorbiaceace family.

Consequently, reference herein to an "angeloyl substituted ingenane or derivative thereof" includes a purified form of one or more angeloyl substituted ingenanes or derivatives thereof or a chemical fraction or extract such as from the sap of a plant of the Euphorbiaceace family, and in particular a species of Euphorbia, and most preferably from E. peplus or botanical or horticultural relatives or variants thereof, wherein the chemical fraction or extract comprises one or more angeloyl substituted ingenanes or derivatives thereof.

Especially preferred angeloyl substituted ingenanes or derivatives thereof contemplated herein are represented by the general Formula (I):—

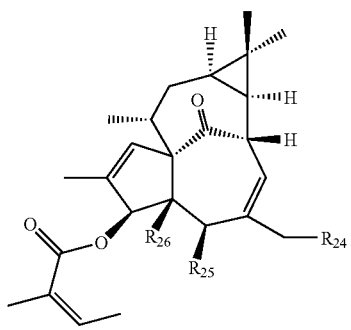

wherein:—
- $R_{24}$, $R_{25}$ and $R_{26}$ are independently selected from hydrogen, OH, $R_{27}$, $R_{28}$, F, Cl, Br, I, CN, $OR_{27}$, $SR_{27}$, $NR_{27}R_{28}$, $N(=O)_2$, $NR_{27}OR_{28}$, $ONR_{27}R_{28}$, $SOR_{27}$, $SO_2R_{27}$, $SO_3R_{27}$, $SONR_{27}R_{28}$, $SO_2NR_{27}R_{28}$, $SO_3NR_{27}R_{28}$, $P(R_{27})_3$, $P(=O)(R_{27})_3$, $Si(R_{27})_3$, $B(R_{27})_2$, $(C=X)R_{29}$ or $X(C=X)R_{29}$ where X is selected from sulfur, oxygen and nitrogen;
- $R_{27}$ and $R_{28}$ are each independently selected from $C_1$-$C_{20}$ alkyl (branched and/or straight chained), $C_1$-$C_{20}$ aryalkyl, $C_3$-$C_8$ cycloalkyl, $C_6$-$C_{14}$ aryl, $C_1$-$C_{14}$ heteroaryl, $C_1$-$C_{14}$ heterocycle, $C_2$-$C_{10}$ alkenyl (branched and/or straight chained), $C_2$-$C_{10}$ alkynyl (branched and/or straight chained), $C_1$-$C_{10}$ heteroarylalkyl, $C_1$-$C_{10}$ alkoxyalkyl, $C_1$-$C_{10}$ haloalkyl, dihaloalkyl, trihaloalkyl, haloalkoxy, $C_1$-$C_{10}$ [CN, $OR_{27}$, $SR_{27}$, $NR_{27}R_{28}$, $N(=O)_2$, $NR_{27}OR_{28}$, $ONR_{27}R_{28}$, $SOR_{27}$, $SO_2R_{27}$, $SO_3R_{27}$, $SONR_{27}R_{28}$, $SO_2NR_{27}R_{28}$, $SO_3NR_{27}R_{28}$, $P(R_{27})_3$, $P(=O)(R_{27})_3$, $Si(R_{27})_3$, $B(R_{27})_2$]alkyl;
- $R_{29}$ is selected from $R_{27}$, $R_{28}$, CN, $COR_{27}$, $CO_2R_{27}$, $OR_{27}$, $SR_{27}$, $NR_{27}R_{28}$, $N(=O)_2$, $NR_{27}OR_{28}$, $ONR_{27}R_{28}$, $SOR_{27}$, $SO_2R_{27}$, $SO_3R_{27}$, $SONR_{27}R_{28}$, $SO_2NR_{27}R_{28}$, $SO_3NR_{27}R_{28}$, $P(R_{27})_3$, $P(=O)(R_{27})_3$, $Si(R_{27})_3$, $B(R_{27})_2$.

In a preferred embodiment, $R_{24}$ is hydrogen, OAcetyl or OH. In a more preferred embodiment, $R_{24}$ is OH.

In another preferred embodiment, $R_{25}$ and $R_{26}$ are OH.

In a most preferred embodiment, the angeloyl substituted ingenane is ingenol-3-angelate which is referred to herein as "PEP005" or a pharmaceutically acceptable salt thereof. Other ingenol angelates contemplated herein include 20-deoxy-ingenol-3-angelate (PEP006), 20-O-acetyl-ingenol-3-angelate (PEP008) or therein pharmaceutically acceptable salts.

As used herein, the term "alkyl" refers to linear or branched chains. The term "haloalkyl" refers to an alkyl group substituted by at least one halogen. Similarly, the term "haloalkoxy" refers to an alkoxy group substituted by at least one halogen. As used herein the term "halogen" refers to fluorine, chlorine, bromine and iodine.

As used herein the term "aryl" refers to aromatic carbocyclic ring systems such as phenyl or naphthyl, anthracenyl, especially phenyl. Suitably, aryl is $C_6$-$C_{14}$ with mono, di- and tri-substitution containing F, Cl, Br, I, $NO_2$, $CF_3$, CN, $OR_1$, $COR_1$, $CO_2R_1$, $NHR_1$, $NR_1R_2$, $NR_1OR_2$, $ONR_1R_2$, $SOR_1$, $SO_2R_1$, $SO_3R_1$, $SONR_1R_2$, $SO_2NR_1R_2$, $SO_3NR_1R_2$, $P(R_1)_3$, $P(=O)(R_1)_3$, $Si(R_1)_3$, $B(R_1)_2$, wherein $R_1$ and $R_2$ are defined above.

The terms "heterocycle", "heterocyclic", "heterocyclic systems" and the like refer to a saturated, unsaturated, or aromatic carbocyclic group having a single ring, multiple fused rings (for example, bicyclic, tricyclic, or other similar bridged ring systems or substituents), or multiple condensed rings, and having at least one heteroatom such as nitrogen, oxygen, or sulfur within at least one of the rings. This term also includes "heteroaryl" which refers to a heterocycle in which at least one ring is aromatic. Any heterocyclic or heteroaryl group can be unsubstituted or optionally substituted with one or more groups, as defined above. Further, bi- or tricyclic heteroaryl moieties may comprise at least one ring, which is either completely, or partially, saturated. Suitable heteroaryl moieties include, but are not limited to, oxazolyl, thiazaoyl, thienyl, furyl, 1-isobenzofuranyl, 3H-pyrrolyl, 2H-pyrrolyl, N-pyrrolyl, imidazolyl, pyrazolyl, isothiazolyl, isooxazolyl, pyridyl, pyrazinyl, pyrimidinyl, pyradazinyl, indolizinyl, isoindolyl, indoyl, indolyl, purinyl, phthalazinyl, 1,2,3-triazolyl, 1,2,4-triazolyl, 1,2,3-oxadiazoyl, 1,2,4-oxadiazolyl, 1,2,5-oxadiazolyl, 1,3,4-oxadiazolyl, 1,2,3,4-oxatriazolyl, 1,2,3,5-oxatriazolyl, 1,3,5-triazinyl, 1,2,4-triazinyl, 1,2,3-triazinyl, azepinyl, oxepinyl, thiepinyl, benzofuranyl, isobenzofuranyl, thionaphthenyl, isothionaphthenyl, indoleninyl, 2-isobenzazolyl, 1,5-pyrindinyl, pyrano[3,4-b]pyrrolyl, isoindazolyl, indoxazinyl, benzoxazolyl, anthranilyl, quinolinyl, isoquinolinyl, cinnolinyl, quinazolinyl, naphthyridinyl, pyrido[3,4-b]pyridinyl, and pyrido[3,2-b]pyridinyl, pyrido[4,3-b]pyridinyl.

As indicated above, particularly preferred angeloyl substituted ingenanes or derivatives thereof include, but are not limited to, ingenol-3-angelate (PEP005), 20-deoxy-ingenol-3-angelate (PEP006), 20-O-acetyl-ingenol-3-angelate (PEP008), or derivatives of the angelates, or pharmaceutically acceptable salts thereof. In a most preferred embodiment, the angeloyl substituted ingenane or derivative thereof is ingenol-3-angelate referred to herein as "PEP005". In any event, any angeloyl substituted ingenane or derivative thereof which induces chemoablation of solid cancer tissue while inducing the generation of cancer-specific T-cells in particular $CD8^+$ T-cells, $CD4^+$ T-cells and/or cancer-specific antibodies may be used in the practice of the present invention.

As used herein, the term "administering directly or proximally to said cancer" should be understood to include administration of the angeloyl substituted ingenanes or derivatives thereof to the cancer per se and/or to the local region of the cancer in the subject. The term "local administration" is used to include, inter alfa, topical i.t., i.l. or p.t. administration of the agent wherein the agent is directly injected or otherwise introduced into the cancer itself and/or the area of cancer growth. Administration of the agent may also be via an artery which substantially feeds the cancer or a local region surrounding or proximal to the cancer such that a relatively high concentration of the agent is accumulated at the site of the cancer. Such administration includes, for example, administration of the agent to the hepatic artery for the treatment of hepatocellular carcinomas. Local administration of the angeloyl substituted ingenanes or derivatives thereof to the cancer includes topical administration to an epithelial or endothelial surface, topical administration to the surface of a cancer which is exposed during surgery or topical administration to the gastrointestinal tract by ingestion.

Hence, the term "local administration" encompasses direct or proximal administration of the angeloyl substituted ingenane to the cancer.

The present invention further contemplates the administration of angeloyl substituted ingenanes or derivatives thereof together with genetic, immunological or cytological therapy to enhance, co-operate and/or synergize with the cancer-specific T-cell response induced by the angeloyl substituted ingenanes or derivatives thereof. Such combination therapy is particularly useful in the prevention of relapse or secondary cancer growth.

The genetic, immunological or cytological therapy may be administered at a distant site to the cancer or it may be provided systemically or directly or proximally (i.e. locally) to the cancer.

The one or more genetic, immunological or cytological therapies or therapeutic agents may be co-administered or sequentially administered with the angeloyl substituted ingenane or derivative thereof. By "co-administered" is meant simultaneous administration in the same formulation or in two different formulations via the same or different routes or sequential administration by the same or different routes. By "sequential" administration is meant a time difference of seconds, minutes, hours or days between the administration of the two agents or treatment protocols. The sequentially administered agents or treatment protocols may be administered in any order.

When the other genetic, immunological or cytological therapeutic agent is co-administered with the angeloyl substituted ingenane or derivative thereof, it is administered at a distant site directly or proximal to the cancer or it may be administered systemically to the subject.

Additional cancer treating regimens may also be employed including radiotherapy, chemotherapy, gene therapy, vaccine therapy, immunotherapy and/or adoptive immunotherapy.

In addition, the present invention encompasses the use of imaging technology to assist in the direct administration of an angeloyl substituted ingenane into a tumor. For example, in one embodiment, the angeloyl substituted ingenane may be injected into the tumor whereby the needle or other administering device is guided by Computed Tomography (CT), Volume Computed Tomography (VCT), Singe-photon Emission Computed Tomography (SPECT) and/or Positron Emission Tomography (PET).

Hence, the present invention contemplates combination therapy comprising the administration of an angeloyl substituted ingenane such as but not limited to PEP005 and a T-cell potentiating agent or therapy which enhances (i.e. potentiates), co-operates and/or synergizes with the cancer-specific T-cells induced following chemoablation. Such agents and therapies include inter alia the administration of a cytokine (e.g. IL-2, IL7, IL-15, GM-CSF), an antibody (e.g. anti-CD40 antibody or anti-CTLA4 antibody), an agent which removes suppressor T-cells, an anti-cancer vaccine (e.g. DC vaccines, vaccines comprising tumor antigens or epitopes, virus vectored cancer vaccines), a T-cell potentiating agent (e.g. CpG) or adoptive immunotherapy.

Suitable agents and therapies for use in combination with an angeloyl substituted ingenane are described in Morcellin et al, *Lancet Oncol* 5:681-689, 2004; Ostrand-Rosenberg, *Cancer Invest* 23(5):413-419, 2005; Banchereau and Palucka, *Nat. Rev. Immunol* 5(4):296-306, 2005; and the references contained therein.

As indicated above, local administration of angeloyl substituted ingenane or derivative thereof treatment may be combined with genetic, immunological or cytological therapy including a cancer vaccine delivered at site distant to the primary tumor being treated.

"Cancer vaccines" may be employed therapeutically or for prophylaxis after primary therapy. The aim of the cancer vaccine is to enhance the level of the cancer-specific T-cells and/or cancer-specific antibodies induced by the angeloyl substituted ingenane or derivative thereof. Several vaccine approaches may be employed, including DC vaccines, virus-vector-based vaccines, vaccines using peptides derived from cancer-associated antigens, vaccines using cancer antigens expressed as recombinant proteins, vaccines using intact irradiated cancer cells including those transduced with co-stimulatory or other antigens, and carbohydrate or glycolipid vaccines. DNA vaccine approaches may also be used (Morcellin et al 2004 supra).

Virus infected allogeneic cancer cell lines, and non-viable extracts of infected cells may be used as cancer vaccines. Virus infection of the cancer cells results in the expression of viral antigens in proximity to cancer-associated antigens and these cancer vaccines are typically immune stimulators. Recombinant virus vector-based vaccines include pox-virus vaccines (MVA, ALVAC, NYVAC, vaccinia), other virus vector-based vaccines such as adenovirus (Basak et al, *Viral Immunol. Summer* 17(2):182-96, 2004). Other vaccines include peptides and DC vaccines (Lonchay et al, *Proc Natl Acad Sci U S A.* 101 *Suppl* 2:14631-8, 2004) and ISCOMs (Maraskovsky et al, *Clin Cancer Res.* 10(8):2879-90, 2004).

In one preferred embodiment, virus vectors such as vaccinia constructs that include a gene coding for a cancer antigen are used as a cancer vaccine.

Peptide epitopes that can be presented by certain human leukocyte antigen (HLA) haplotypes (e.g., HLA-A2) have been derived from cancer-associated antigens and may also form the basis of a cancer vaccine. Peptide vaccines have the potential to induce immune responses in vivo that are specific for epitopes on the cancer cells and, therefore, have therapeutic potential.

Reference herein to a "cancer antigen" or an antigen from a cancer cell or a peptide epitope from a cancer antigen includes 707-AP (707 alanine proline), AFP (alpha (α)-fetoprotein), AIM-2 (interferon-inducible protein absent in melanoma 2), ART-4 (adenocarcinoma antigen recognized by T-cells 4), GAGE (B antigen), β-catenin/m (β-catenin/mutated),Bcr-abl (breakpoint cluster region-Abelson), β-HCG (β-human chorionic gonadotropin), Beta$_2$ (β$_2$)-microglobulin, CA-125 (carbohydrate antigen 125), CA 15-3 (carbohydrate antigen 15-3), CA 19-9 (Carbohydrate antigen 19-9), CAMEL (CTL-recognized antigen on melanoma), CAP-1 (carcinoembryonic antigen peptide-1), CASP-8 (caspase-8), CDC27m (cell-division cycle 27 mutated), CDK4/m (cycline-dependent kinase 4 mutated), CEA (carcinoembryonic antigen), CLCA2 (calcium-activated chloride channel-2), CT (cancer/testis (antigen)), Cyp-B (cyclophilin B), cytochrome P450 isoform 1B1, DAM (differentiation antigen melanoma (the epitopes of DAM-6 and DAM-10 are equivalent, but the gene sequences are different. DAM-6 is also called MAGE-B2 and DAM-10 is also called MAGE-B1), ELF2M (elongation factor 2 mutated), Ep-CAM (epithelial cell adhesion molecule), EphA2, 3 (Ephrin type-A receptor 2, 3), ETV6-AML1 (Ets variant gene 6/acute myeloid leukemia 1 gene ETS), FGF-5 (Fibroblast growth factor-5), FN (fibronectin), G250 (glycoprotein 250), GAGE (G antigen), GnT-V (N-acetylglucosaminyltransferase V), Gp100 (glycoprotein 100 kD), HAGE (helicose antigen), HER-2/neu (human epidermal receptor-2/neurological), HLA-A*0201-R170I (arginine (R) to isoleucine (I) exchange at residue 170 of the α-helix of the α2-domain in the HLA-A2 gene), HPV-E7 (human papilloma virus E7), HSP70-2M (heat shock protein 70-2 mutated), HST-2 (human signet ring cancer-2), hTERT or hTRT (human telomerase reverse transcriptase), iCE (intestinal carboxyl esterase), IL-13Rα2 (interleukin 13 receptor α2 chain), KIAA0205, Lactate dehydrogenase, LAGE (L antigen), LDLR/FUT (low density lipid receptor/GDP-L-fucose: β-D-galactosidase 2-α-Lfucosyltransferase), MAGE (melanoma antigen), MART-1/Melan-A (melanoma antigen recognized by T-cells-1/Melanoma antigen A), MART-2

(melanoma Ag recognized by T-cells-2), M-CSF (macrophage colony-stimulating factor gene), MDM2, MC1R (melanocortin 1 receptor), Myosin/m (myosin mutated), MUC1 (mucin 1), MUC 2 (mucin 2), MUM-1, -2, -3 (melanoma ubiquitous mutated 1, 2, 3), NA88-A (NA cDNA clone of patient M88), Neo-PAP (Neo-poly(A) polymerase), NPM/ALK (nucleophosmin/anaplastic lymphoma kinase fusion protein), NY-ESO-1 (New York-esophageous 1), OA1 (ocular albinism type 1 protein), OGT (O-linked N-acetylglucosamine transferase gene), OS-9, P15 (protein 15), p190 minor bcr-abl (protein of 190 KD bcr-abl), Pml/RAR$\alpha$ (promyelocytic leukemia/retinoic acid receptor $\alpha$PRAME (preferentially expressed antigen of melanoma), PSA (prostate-specific antigen), PSM (prostate-specific membrane antigen), PTPRK (receptor-type protein-tyrosine phosphatase kappa), RAGE (renal antigen), RU1 or RU2 (renal ubiquitous 1 or 2), SAGE (sarcoma antigen), SART-1 or SART-3 (squamous antigen rejecting cancer 1 or 3), SSX-2 (synovial sarcoma, X breakpoint 2), Survivin-2B (intron 2-retaining survivin), SYT/SSX (synaptotagmin I/synovial sarcoma, X fusion protein), TEL/AML1 (translocation Ets-family leukemia/acute myeloid leukemia 1), TGF$\beta$RII (transforming growth factor $\beta$ receptor 2), TPI/m (triosephosphate isomerase mutated), TRAG-3 (taxol resistant associated protein 3), TRG (testin-related gene), TRP-1 (tyrosinase related protein 1, or gp75), TRP-2 (tyrosinase related protein 2), TRP-2/INT2 (TRP-2/intron 2), TRP-2/6b (TRP-2/novel exon 6b) and WT1 (Wilms' cancer gene).

A range of other cancer antigens would be readily ascertained by one of skill in the art and, accordingly, the present invention should not be considered in any way limited to the specific cancer antigens exemplified above.

The present invention further contemplates a pharmaceutical composition comprising an angeloyl substituted ingenane or derivative thereof, capable of inducing ablation of cancer tissue and stimulating the generation of cancer-specific CD8$^+$ T-cells and optionally CD4$^+$ T-cells together with a pharmaceutically acceptable carrier or diluent. Alternatively, the pharmaceutical composition is comprised within a multi-compartmental pharmaceutical formulation comprising in one compartment the angeloyl substituted ingenane or derivative thereof and in another compartment an agent capable of enhancing the level of cancer-specific T-cells induced by the angeloyl substituted ingenane or derivative thereof.

Pharmaceutically acceptable carriers and/or diluents include any and all solvents, dispersion media, coatings, antibacterial and anti-fungal agents, isotonic and absorption delaying agents and the like. The use of such media and agents for pharmaceutically active substances is well known in the art and except insofar as any conventional media or agent is incompatible with the modulator; their use in the therapeutic compositions is contemplated. Supplementary active compounds can also be incorporated into the compositions.

In one embodiment, the pharmaceutical composition comprises a form suitable for local administration which includes topical, i.l. or p.t. injection or other form of application or administration.

Composition forms include sterile aqueous solutions or other solutions and sterile powders for the extemporaneous preparation of sterile injectable solutions. It must be stable under the conditions of manufacture and storage and must be preserved against the contaminating action of microorganisms such as bacteria and fungi. The carrier can be a solvent or dilution medium comprising, for example, water, ethanol, polyol (for example, glycerol, propylene glycol and liquid polyethylene glycol, and the like), suitable mixtures thereof and vegetable oils. The proper fluidity can be maintained, for example, by the use of superfactants. Microorganisms in the composition may be controlled by various anti-bacterial and anti-fungal agents, for example, parabens, chlorobutanol, phenol, sorbic acid, thirmerosal and the like. In many cases, it will be preferable to include isotonic agents, for example, sugars or sodium chloride. Prolonged absorption of the injectable compositions can be brought about by the use in the compositions of agents delaying absorption, for example, aluminium monostearate and gelatin, and PEG400. A composition for local administration may be applied to or proximal to a cancer surface (i.e. topical application) or may be delivered by i.t., i.l. or p.t. injection or other form of administration.

In a local formulation, the active agent may be suspended within a cream ointment, wax or other liquid or semi-liquid solution such that topical application of the cream or ointment or lotion or wax or liquid solution results in the introduction of the active agent to or on or within a biological surface in the subject. The term "biological surface" as used herein, contemplates any surface on or within the organism. Examples of "biological surfaces" to which the topical compositions of the present invention may be applied include any epithelial or endothelial surface such as the skin, respiratory tract, gastrointestinal tract and genitourinary tract. The term "local administration" includes topical, i.l., i.t. and p.t. administration and as well as administration to fissures or cracks in a biological surface. As set out supra "local" administration should also be considered to include topical administration to a biological surface which has been exposed or made accessible via surgery to the subject. For example, "topical administration" should be understood to include administration to the surface of a cancer which may not normally be exposed or accessible (e.g. the cancer is present within the body of the subject) wherein the surface of the cancer becomes exposed or accessible as a result of surgery on the subject or the tumor is accessed by needle.

A "local formulation" especially for topical application typically comprises a pharmaceutically acceptable carrier for topical treatment, which includes, but is not limited to, a neutral sterile cream, a base cream, a lotion, a wax, a gel, a jelly, an ointment, an aerosol, a patch, powders, and/or a combination thereof.

The present invention covers, therefore, ointments, creams, lotions, waxes, gels and pastes.

Ointments are semi-solid preparations that are typically based on petrolatum or other petroleum derivatives. The specific ointment base to be used, as will be appreciated by those skilled in the art, is one that will provide for optimum drug delivery, and, preferably, will provide for other desired characteristics as well as, e.g. emolliency or the like. As with other carriers or vehicles, an ointment base should be inert, stable, non-irritating and non-sensitizing. Ointment bases may be grouped in four classes: oleaginous bases; emulsifiable bases; emulsion bases; and water-soluble bases. Oleaginous ointment bases include, for example, vegetable oils, fats obtained from animals, and semi-solid hydrocarbons obtained from petroleum. Emulsifiable ointment bases, also known as absorbent ointment bases, contain little or no water and include, for example, hydroxystearin sulfate, anhydrous lanolin, and hydrophilic petrolatum. Emulsion ointment bases are either water-in-oil (W/O) emulsions or oil-in-water (O/W) emulsions, and include, for example, cetyl alcohol, glyceryl monostearate, lanolin, and stearic acid. Preferred water-soluble ointment bases are prepared from polyethylene glycols of varying molecular weight.

Creams are viscous liquids or semi-solid emulsions, either oil-in-water or water-in-oil. Cream bases are water-washable, and contain an oil phase, an emulsifier, and an aqueous phase. The oil phase, also called the "internal" phase, is generally comprised of petrolatum and a fatty alcohol such as cetyl or stearyl alcohol. The aqueous phase usually, although not necessarily, exceeds the oil phase in volume, and generally contains a humectant. The emulsifier in a cream formulation is generally a non-ionic, anionic, cationic, or amphoteric surfactant.

Lotions are preparations to be applied to the skin surface without friction, and are typically liquid or semi-liquid preparations in which solid particles, including the active agent, are present in a water or alcohol base. Lotions are usually suspensions of solids, and preferably, for the present purpose, comprise a liquid oily emulsion of the oil-in-water type. Lotions and gels are preferred formulations herein for treating large body areas, because of the ease of applying a more fluid composition. It is generally necessary that the insoluble matter in a lotion be finely divided. Lotions will typically contain suspending agents to produce better dispersions as well as compounds useful for localizing and holding the active agent in contact with the skin, e.g. methylcellulose, sodium carboxymethylcellulose, or the like.

Pastes are semi-solid dosage forms in which the active agent is suspended in a suitable base. Depending on the nature of the base, pastes are divided between fatty pastes or those made from a single-phase aqueous gels. The base in a fatty paste is generally petrolatum, hydrophilic petrolatum, or the like. The pastes made from single-phase aqueous gels generally incorporate carboxymethylcellulose or the like as a base.

The present invention is further described by the following non-limiting examples.

Example 1

Induction of Functional Anti-Cancer CD8+ T-Cells by PEP005 Treatment of Established Tumors Introduction This study used the B16 melanoma and the Lewis lung carcinoma lines, which are both transfected with a model tumor antigen, ovalbumin (OVA). CD8+ T-cell responses against the ovalbumin CD8+ T-cell epitope, SIINFEKL [SEQ ID NO:2], can be readily detected using IFNγ ELISPOT assays and are also known to protect mice from challenge against B16-OVA and Lewis lung-OVA.

The aims of this study were to (i) test whether topical tumors treated with PEP005 induce SIINFEKL [SEQ ID NO:2]-specific CD8+ T-cell responses in the B16-OVA and Lewis lung-OVA murine tumor models, and (ii) to test whether PEP005 treatment of primary tumors can protect against growth of distant tumors.

Tumor Cell Lines

B16 and B16 cells stably expressing ovalbumin (B16-OVA) were grown s.c. in C57BL/6 mice as described previously (Ogbourne et al, *Cancer Res* 64:2833-2839, 2004; Anraku et al, *J Virol* 76:3791-3799, 2002). Lung metastases were established as described (Zeh et al, *J Immunol* 162:989-994, 1999). Lewis lung-OVA (Nelson et al, *J Immunol* 166: 5557-5566, 2001) were grown s.c. in C57BL/6 as described (Lenarczyk et al, *Vaccine* 22:963-974, 2004).

PEP005 Therapy

Tumors were treated by topical or intratumoral (i.t.) injection (using a 26 gauge needle) of (i) PEP0005 dissolved in acetone and then RPMI 1640 (final concentration of acetone 4%), or (ii) PEP005 formulated in PEG400.

ELISPOT Assay

Mouse splenocytes were analyzed by ex vivo IFNγ ELISPOT essentially as described previously (Le et al, *Vaccine* 19:4669-4675, 2001), but using MultiScreen-IP plates (Millipore) and 25 IU/ml of recombinant human IL-2 (Cetus).

Statistical Methods

Parametric Student's t-test for normally distributed data and Wilcoxon Rank sum test for data not normally distributed. Log rank test for Kaplin-Meier curves.

Results

SIINFEKL-Specific CD8+ T-Cell Induction After Topical PEP005 Treatment of B16-OVA Following three topical applications of PEP005 to established s.c. B16-OVA tumors on C57/BL6 mice, the number of SIINFEKL [SEQ ID NO:2]-specific CD8+ T-cell induced were measured using IFNγ ELISPOT. As controls, the SIINFEKL [SEQ ID NO:2] specific CM+ T-cell induced following (i) PEP005 treatment without tumor, (ii) mock treatment of B16 tumors and (iii) naïve mice (no PEP005 or tumor), were also tested. Mice receiving PEP005 without tumor (FIG. 1A) or vehicle alone on tumors (FIG. 1B) showed (on average) no significant responses above the five spots/$10^6$ splenocytes considered to be the limit of detection of this assay (see summary FIG. 1D, labeled (A) and (B) and also the number of spots seen in naïve animals (FIG. 1D, labeled 'no PEP005, no tumor'). Mice with treated B16-OVA tumors showed some weak variable responses to SIINFEKL [SEQ ID NO:2] (FIG. 1C). Due to the small number (n=4) of cured mice these later responses were not significantly different from those seen in A or B. Only when results from all the mice in groups A and B are combined and compared with C do the responses from cured B16-OVA mice approach significant difference (p=0.058) over the negative control animals, indicating that PEP005 treatment induces tumor specific CD8+ T-cells.

Figure 2:
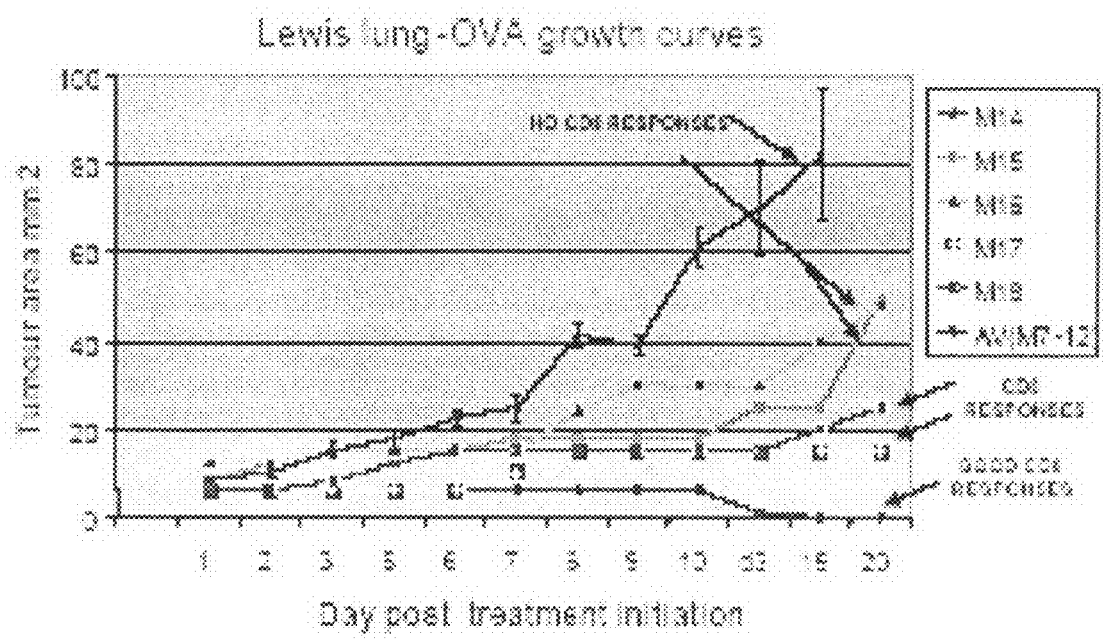
FIG. 2 is a graphical representation showing growth of individual Lewis lung-OVA tumors (10-20 mm² at treatment) in individual mice treated topically with PEP005. See FIG. 1 for CD8⁺ T-cell responses.
Figure 3:
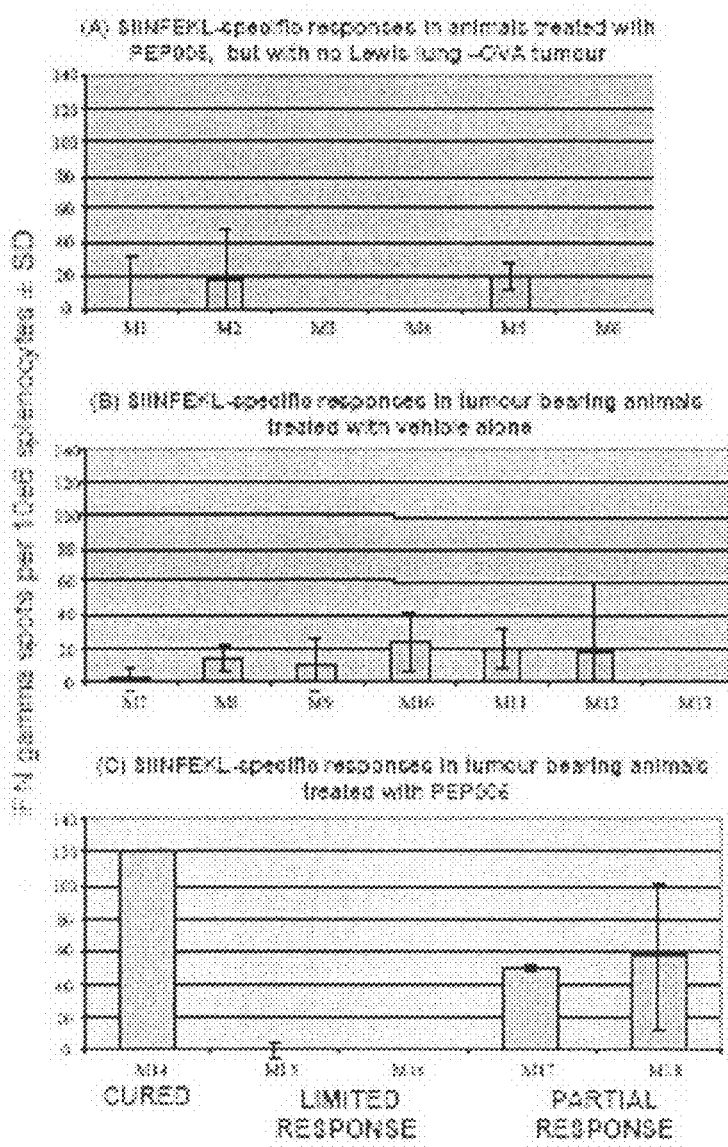
FIGS. 3A to C are graphical representations showing ELISPOT CD8⁺ T-cell responses from individual mice that were treated with PEP005 (A), whose tumors were treated topically with vehicle (B), and whose tumors were treated topically with PEP005 (C). Tumor growth for these mice is shown in FIG. 2.

SIINFEKL-Specific CD8+ T-Cell Induction After Topical PEP005 Treatment of Lewis Lung-OVA Lewis lung-OVA tumors were established on five C57/B16 mice; when they had reached 10-20 mm$^2$, they were treated topically with PEP005. Of the five tumors treated topically with PEP005, only one Lewis lung-OVA tumor was cured (M14, FIG. 2), two animals showed a partial response (M17, 18) and two showed a limited response (M15, 16) to the treatment. A parallel group of tumor-bearing mice (M7-12) were treated (vehicle only) and grew rapidly as expected with mean size±SD shown (FIG. 2, V(M7-12)). ELISPOT analysis of SIINFEKL [SEQ ID NO:2]-specific CD8+ T-cell responses from individual mice are shown in FIG. 3. Mice receiving topical PEP005 but without tumors showed no significant CD8+ T-cell responses (mean for all mice is 6.3±9.8 (SD) spots per $10^6$ splenocytes) (FIG. 3A). The sensitivity of this assay is about five spots per $10^6$ splenocytes. Mice with large tumor burdens also showed poor responses (mean for all mice is 12.5±9.2 (SD) spots per $10^6$ splenocytes) (FIG. 3B). Animals with tumors that had been treated showed a range of responses that correlated with the effectiveness of the treatment. The animal in which the tumor appeared cured at 2-3 weeks showed the highest CD8+ T-cell response, the two that showed partial responses had less CD8+ T-cell responses, and the two animals that showed limited responses showing no detectable CD8+ T-cell responses (FIG. 3C). Thus, again PEP005 treatment was associated with induction of anti-cancer CD8+ T-cells.

Figure 4:
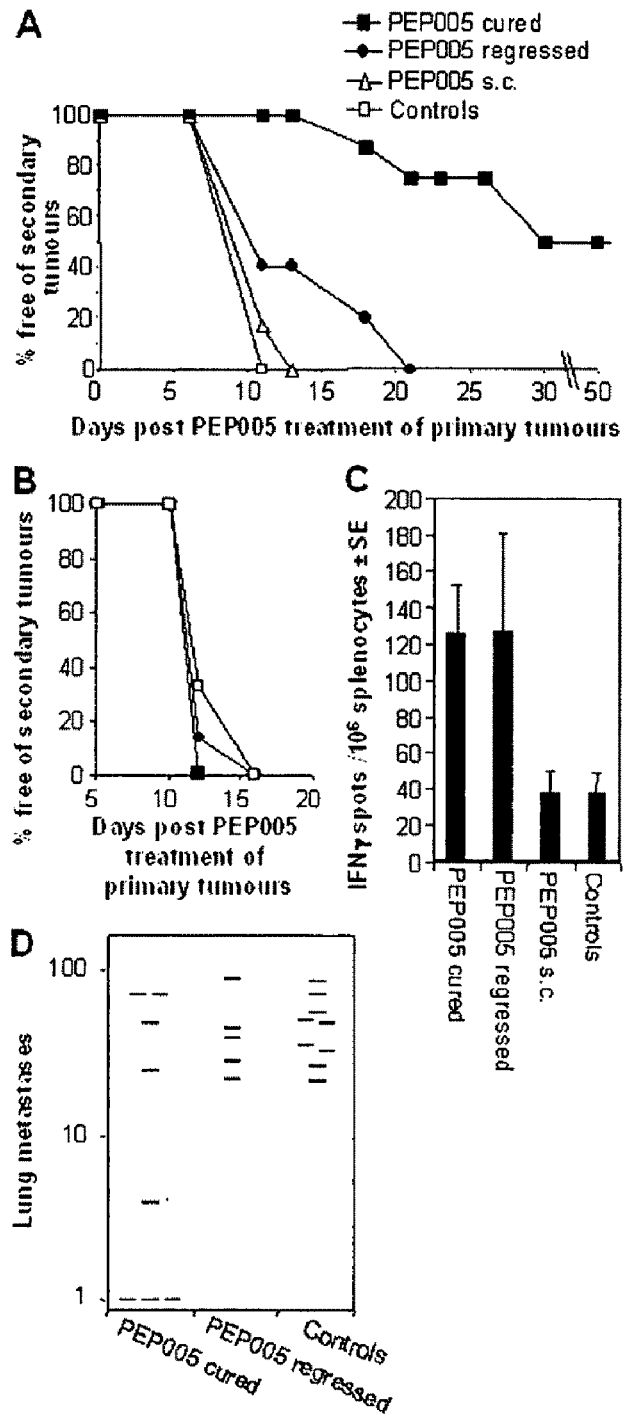
FIGS. 4A to D are graphical representations showing protection against secondary tumors following cure of primary tumors with PEP005. (A) C57BL/6 mice received $5\times10^5$ Lewis lung-OVA s.c. on the back on day less 7 (d−7). When these primary tumors had reached an average 13.6 mm²±1.8 SE (range 10-25 mm²) on d0 they were treated once with 16 µg of PEP005 delivered i.t. In eight mice these primary tumors were cured, and these mice received $5\times10^5$ Lewis lung-OVA s.c. on d4 on the opposite flank from the primary tumors. The emergence of these secondary tumors was monitored over time (PEP005 cured). In a parallel group of animals (n=5) PEP005 treatment regressed the primary tumors, but after 11-13 days the primary tumors re-emerged. These animals also received secondary tumors as above and their emergence was again monitored over time (PEP005 regressed). Two control groups were included. One group (n=6) received no primary tumors, but was treated s.c. with PEP005 and received secondary tumors on the opposite flank (white triangles, PEP005 s.c.). The second control group (n=8) also received no primary tumors, was not treated with PEP005, and received secondary tumors as above (Controls). (B) PEP005-mediated cure of Lewis lung-OVA primary tumors did not reduce the growth of secondary tumors in Foxnl$^{nu}$ mice. The experiment in (A) was repeated in Foxnl$^{nu}$ mice; PEP005 cured (n=4), PEP005 regressed (n=7), Control (n=7). A PEP005 s.c. group was not included. (C) Treatment of primary Lewis lung-OVA with PEP005 induced SIINFEKL-specific CD8⁺ T-cell responses using IFNγ ELISPOT when the secondary tumors had emerged or on d50. (D) Reduced growth of B16-OVA lung metastases following successful treatment of s.c. B16-OVA tumors with PEP005. C57BL/6 mice received $5\times10^5$ B16-OVA s.c. on the back on d−6. When these primary tumors had reached 10-20 mm² on d0, they were treated once with 18 µg of PEP005 delivered i.t., which cured the tumors in eight mice (PEP005 cured) and regressed the tumors in five mice (PEP005 regressed). Controls as above. Secondary B16-OVA ($10^5$) were injected i.v. on d6 and animals were sacrificed on d27 and lung metastases counted.

PEP005-Medicated Cure of Lewis Lung-OVA Tumors Protected Against Challenge with Lewis Lung-OVA It was first sought to determine whether PEP005 treatment of established tumors could induce protective responses that were capable of rejecting a subsequent challenge with the same tumor. C57BL/6 mice were inoculated s.c. with Lewis lung-OVA tumors and when these tumors (nominally referred to as primary tumors) had reached a mean diameter of 13.6 mm$^2$+SE 1.8 they were treated on d0 by i.t. injection of PEP005. On d4 a second inoculation of Lewis lung-OVA cells was administered s.c. on the opposite flank of the animals (nominally referred to as secondary tumors). In mice where PEP005 treatment cured the primary tumor (n=8), emergence of the secondary tumors was significantly delayed (log rank statistic p=0.002), with secondary tumors failing to appear in 50% of animals (FIG. 4A, PEP005 cured). In contrast, by d11-d13 secondary tumors emerged in all control animals, which had received no primary tumors no PEP005 treatment (FIG. 4A, Controls). In animals (n=5) where PEP005 treatment regressed but failed to cure the primary tumors (with primary tumors re-emerging 11-13 days after treatment), the growth of the secondaries was slightly delayed (FIG. 4A, PEP005 regressed), although this was not significant. In animals without primary tumors, injection of PEP005 s.c. at a site distant from the secondary tumors failed to reduce the growth of the secondary tumors (FIG. 4A, PEP005 s.c.), illustrating that drug treatment per se four days prior to injection of the secondary tumors did not affect the growth of the secondary tumors. This experiment demonstrated that successful treatment of primary tumors with PEP005 was able to mediate significant protection against a subsequent challenge with the same tumor.

When the experiment shown in FIG. 4A was repeated in Foxnl$^{nu}$ mice, no protective effect against secondary challenge was evident following PEP005-mediated cure of primary tumors (FIG. 4B). These mice cannot generate T-cell responses, suggesting that the protective effect observed in FIG. 4A was due to the generation of systemic cancer-specific T-cells.

Tumor Specific CD8$^+$ T-Cells

The central role of CD8$^+$ T-cells in mediating protection against tumor challenge in these models is well established (Machlenkin et al, *Clin Cancer Res* 11:4955-4961, 2005; Lenarcyzk et al 2004 supra; Anraku et al 2002 supra; Thomson et al, *J Immunol* 157:822-826, 1996; McAllister et al, *J Virol* 74:9197-9205, 2000; (Zeh et al, 1999 supra) suggesting that PEP005 treatment of primary tumors had induced anti-cancer CD8$^+$ T-cells. Expression of ovalbumin (OVA) in the Lewis lung-OVA tumors provides a simple reporter system for measuring anti-cancer CD8$^+$ T-cell induction by measuring SIINFEKL [SEQ ID NO:2] responses with an IFNγ ELISPOT assay. The mice in which primary tumors were cured by PEP005 treatment had significantly more SIINFEKL [SEQ ID NO:2]-specific CD8$^+$ T-cells than control animals (p=0.008, unpaired t-Test) (FIG. 4C, PEP005 cured). Animals in which PEP005-treated tumors re-emerged showed similar SIINFEKL [SEQ ID NO:2]-specific CD8$^+$ T-cell numbers, but due to increased mouse to mouse variation this only approached significance (p=0.07) (FIG. 4C, PEP006 regressed). PEP005 injected s.c. (rather than into a tumor) failed to increase the number of SIINFEKL [SEQ ID NO:2]-specific CD8$^+$ T-cell numbers compared to untreated control animals (FIG. 4C, PEP005 s.c. and Controls, respectively). These results illustrate that PEP005 treatment of tumors generated tumor-specific CD8$^+$ T-cells.

The B16-OVA Melanoma Lung Metastasis Model

To illustrate that the PEP005-mediated cure of primary tumors was able to inhibit the growth of secondaries in a different tumor system, the B16-OVA lung metastasis model was used. The PEP005-mediated cure of established 10-20 mm$^2$ s.c. primary B16-OVA tumors was again able to reduce significantly (Wilcoxon Signed Rank test, p=0.046) the number of lung metastases given to the animals i.v. six days after PEP005 treatment (FIG. 4D, PEP005 cured). Partial regression of the primary tumors by PEP005 again failed to inhibit significantly the growth of lung metastases (FIG. 4D, PEP005 regressed).

The B16 Lung Metastasis Model

Figure 5:
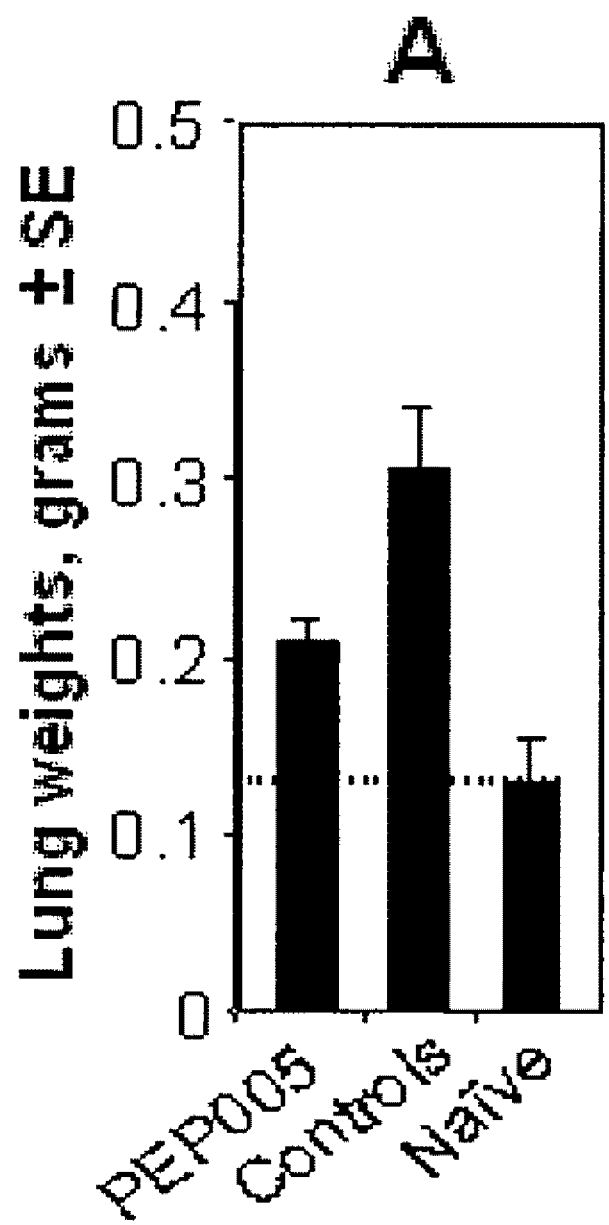
FIG. 5 is a graphical representation showing the treatment of s.c. B16 tumors with PEP005 reduced growth B16 lung metastases. C57BL/6 mice (n=7) were injected with $10^6$ B16 cells s.c. and $5\times10^4$ B16 cell i.v. on d−2. On d0 the s.c. tumors had reached an average 21.8 mm²+SE 2.4 and were cured with 25 µg of i.t. PEP005 formulated with PEG400. On d18 the mice were euthanazed and lung weights determined (PEP005). Control mice received only i.v. B16 and naïve mice received no tumors (n=6 per group).

The activity of PEP005-mediated cure of primary tumors was assessed in a more robust model using B16 tumors rather than B16-OVA tumors and where primary tumors and lung metastases were both established prior to PEP005 treatment. When the primary tumors had reached 21.8+SE 2.4 they were cured with i.t. PEP005 injection. The lung weights were determined on d18 and were significantly (p=0.023, unpaired t-Test) lighter in these animals compared to controls (FIG. 5A, PEP005 cured and Controls). After subtracting the weight of tumor free lungs (FIG. 5A, naïve, dotted line), this represented a reduction in lung tumor burden of over 50%. This experiment illustrated that PEP005-mediated cure of primary tumors resulted in significant regression of multiple metastases established at a distant site.

Conclusion

These data illustrate that PEP005 treatment of cancer cells leads to the induction of anti-cancer CD8$^+$ T-cells which are functionally able to inhibit the growth of distant secondary tumors.

Example 2

PEP005 and DC Therapy Synergize to Improve Cure of Primary Tumors

To determine whether PEP005 (ingenol-3-angelate) treatment could synergize with (i) vaccine-induced anti-cancer CD4$^+$ T-cells/antibodies and/or (ii) DC vaccine-induced anti-cancer CD8$^+$ T-cells, topical PEP005 treatment was combined with vaccination using (i) B16 lysate emulsified in Montanide ISA 720 adjuvant (M720/B16) and (ii) DC2.4 cells sensitized with TRP-2 peptide, SVYDFFVWL [SEQ ID NO:1] (a dominant CD8$^+$ T-cell epitope for anti-B16 CM$^+$ T-cells) and activated with LPS (Camporeale et al, *Can Res* 63:3688, 2003) (DC). The latter group also received IL-2 to maintain the vaccine induced T-cells. The topical PEP005 dose (10 μg/mouse) was known not to be sufficient to cure most B16 tumors of reasonable size. Thus, this experiment sought to determine whether improvements in B16 cure rate could be achieved when sub-optimal topical PEP005 treatment was combined with other immune-based therapies.

B16 tumors were injected 2×10$^4$ s.c. in groups (n=5 per group) of C57BL/6 mice and after 12 days (d0) had reached 8-12 mm$^2$ in size. The groups of animal received the following treatments:

Group 1

Control: Control receiving no treatment.

Group 2

PEP005: On d0, the tumors in this group were treated topically with PEP005, 10 μg/mouse in 10 μl isopropanol gel.

Group 3

PEP005+M720: On d−5 (day minus 5), the animals had received Montanide ISA 720 adjuvant (M720) emulsified 7:3 v:v (Elliott et al, *Vaccine*. 17(15-16):2009-2019, 1999) with water (volume 100 μl/mouse s.c.) and on d0, the tumors in this group were treated topically with PEP005.

Group 4

PEP005+M720/B16: On d−5, the animals had received Montanide ISA 720 adjuvant (M720) emulsified 7:3 v:v (Elliott et al, 1999 supra) with B16 cell lysate (3×10$^5$ B16 cells per mouse s.c., volume 100 μl/mouse) and on d0, the tumors in this group were treated topically with PEP005. A modality was known to induce CD4+ T-cells specific for B16.

Group 5

PEP005+M720/B16+DC+IL-2: On d0, the tumors in this group were treated topically with PEP005 and had been given M720/B16 as for Group 4. The group also received on d0 DC in the form of a DC cell line, DC2.4. These cells were (i) sensitized with TRP-2 peptide, SVYDFFVWL [SEQ ID NO:1] (40 μg/ml 1 h, 37° C.), (ii) activated with LPS (a further 5 hr incubation at 37° C. using 1 μg/ml $E.$ $coli$ 055:B5, Sigma), (iii) irradiated (3000 rads), washed and then injected i.v. ($5 \times 10^6$/mouse). The animals also received rhIL-2 $5 \times 10^4$ IU twice daily/mouse from d1 to d5 intra-peritoneally.

Group 6

PEP005+DCAL-2: As for Group 5 without M720/B16.

Figure 6:
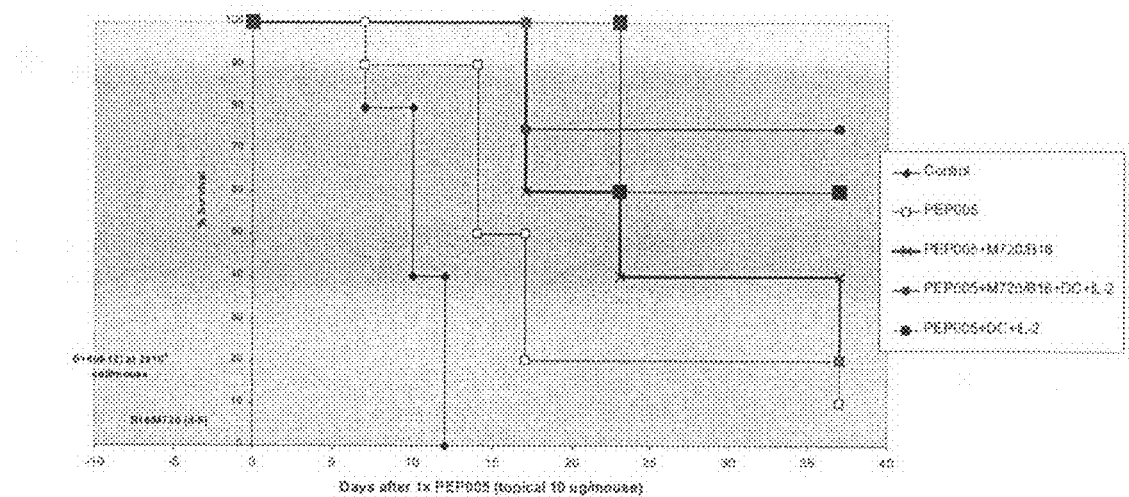
FIG. 6 is a graphical representation of a Kaplan-Meier curve showing PEP005 and DC+IL-2 therapy synergize to improve cure of primary tumors.

The PEP005 group and the PEP005+M720 group gave essentially identical results and were treated as a single group (PEP005/PEP005+M720, n=10) for statistical purposes (FIG. 6, PEP005). As expected the topical application of 10 μg PEP005 had a high failure rate with 90% of treated tumors re-emerging and ultimately requiring the animals to be killed (FIG. 6, PEP005). PEP005+M720/B16 vaccination had a marginal effect that was not significant over PEP005/PEP005+M720 treatment (log Rank statistic, p=0.21). M720/B16 vaccination on top of PEP005+DC+IL-2 therapy (PEP005+M720/B16+DC+IL-2) also showed no significant activity over PEP005+DC+IL-2 therapy.

The PEP005 plus DC+IL-2 therapy resulted in the cure of 60% of the tumors and this was significantly different from the PEP005 group (FIG. 6, p=0.022, PEP005+DC+IL-2 and PEP005/PEP005+M720). The PEP005 plus M720/B16+DC+IL-2 therapy resulted in a 75% cure and this was again significantly different from the PEP005 group (p=0.026, PEP005+M720/B16+DCAL-2 and PEP005/PEP005+M720).

Figure 7:
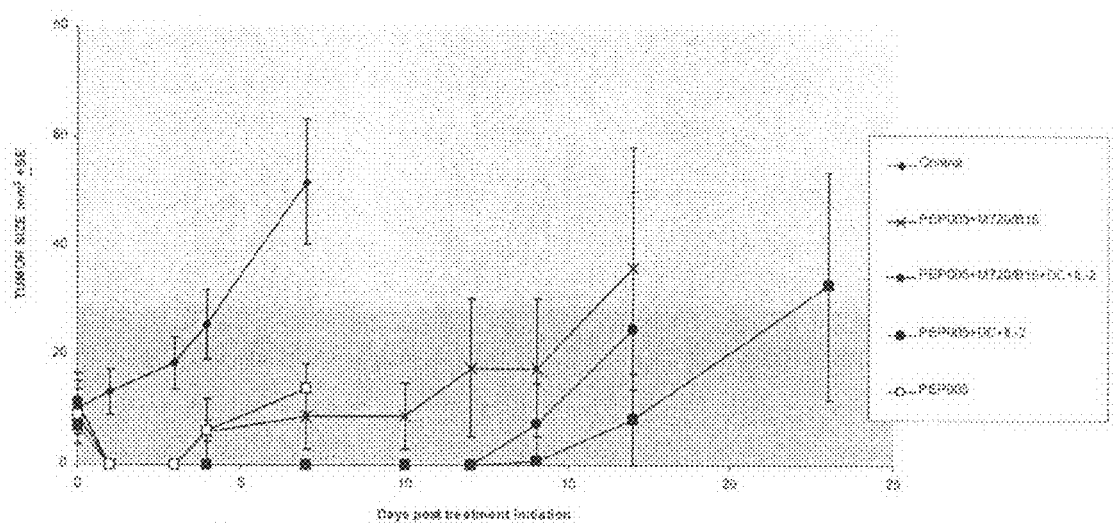
FIG. 7 is a graphical representation showing a growth curve for the same data as shown in FIG. 6. Each line terminates as the first animal in that group is culled because the tumor has reached 100 mm².

The growth curves (FIG. 7) illustrate the substantial delay in tumor growth afforded by DC therapy over PEP005 treatment. All PEP005 treated tumors were regressed by treatment to below detectable size. The tumor in the PEP005 group became visible d4-5, whereas in the DC treated groups tumors emerged d14 (FIG. 7).

The results show that topical PEP005 therapy synergizes with DC+IL-2 therapy to increase the cure rate of the PEP005 treated primary tumors.

Example 3

PEP005 and DC Therapy Synergize to Improve Cure of Primary Tumors

To determine whether PEP005 treatment could synergize with (i) vaccine-induced anti-cancer CD4 T-cells/antibodies and/or (ii) vaccine-induced anti-cancer CD8+ T-cells, topical PEP005 treatment was combined with vaccination using (i) B16 lysate emulsified in Montanide ISA 720 adjuvant (M720/B16) and (ii) DC2.4 cells sensitized with TRP-2 peptide, SVYDFFVWL [SEQ ID NO:1] and activated with LPS (DC). The latter group also received IL-2 to maintain the vaccine induced T-cells. The topical PEP005 dose (15 μg/ml) did not cure most B16 tumors that are 26-30 mm² in size. This experiment sought to determine whether improvements in B16 cure rate could be achieved when sub-optimal topical PEP005 treatment was combined with other immune-based therapies. This experiment differed from that described in Example 2 in that treatment was initiated when tumors were slightly larger and the M720/B16 vaccine was given d0 not d−5, and the dose of B16 cells in that vaccine was increased 10-fold.

B16 tumors were injected $2 \times 10^6$ s.c. into C57BL/6 mice on d−3 and on d0 when the tumors had reached an average size of 26-30 mm², the groups of animal received the following treatments.

Group 1 (n=6)

PEP005: (15 μg/mouse in 15 μl of isopropanol gel, 1× topical) given d0.

Group 2 (n=6)

PEP005+DCAL-2: PEP005 (as above) plus DC2.4 cells which were (i) sensitized with TRP-2 peptide, SVYDFFVWL [SEQ ID NO:1] (40 μg/ml 1 h, 37° C.), (ii) activated with LPS (a further 4 hr incubation at 37° C. using 1 μg/ml $E.$ $coli$ 055:B5, Sigma), (iii) irradiated (3000 rads), washed and then injected i.v. ($2 \times 10^6$/mouse) on d0. This method stimulates epitope-specific CD8+ T-cells. The animals also received rhIL-2 at $5 \times 10^4$ IU given twice daily per mouse from d1 to d4 i.p.

Group 3 (n=6)

DC+IL-2: Received the DC2.4 and IL-2 treatment as for Group 2, but without PEP005 treatment.

Group 4 (n=6)

PEP005+DCAL-2+M720/B16: This group received the same treatment as Group 2 plus on d0 the animals received Montanide ISA 720 adjuvant (M720) emulsified 7:3 v:v (Elliott et al, 1999 supra) with B16 cell lysate ($3 \times 10^6$ B16 cells per mouse s.c., volume 100 μl/mouse).

Group 5 (n=6)

DC+IL-2+M720/B16: This group received the same treatment as Group 3 plus the M720/B16 vaccine described for Group 4.

Group 6 (n=5)

Control: This group received no treatment.

Figure 8:
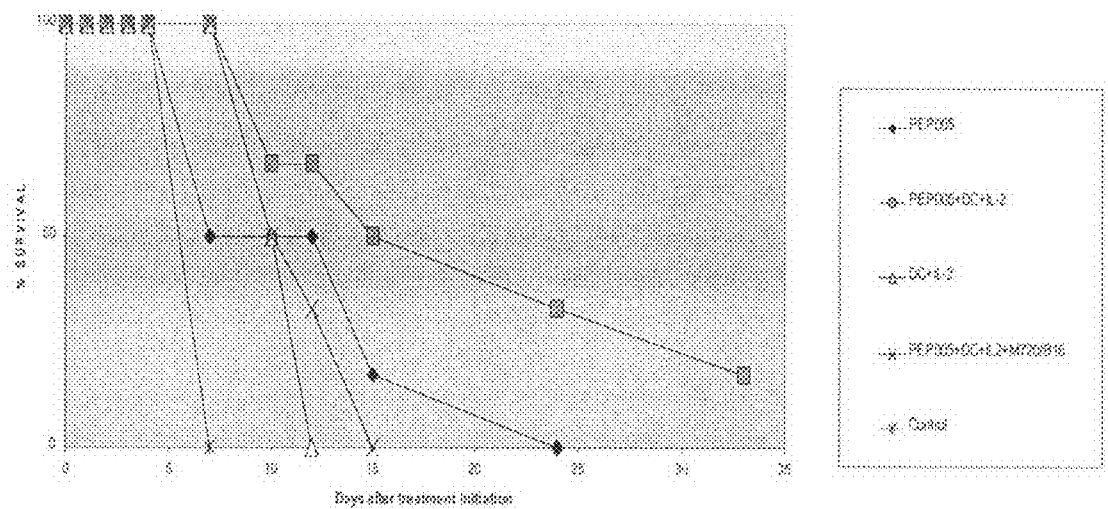
FIG. 8 is a Kaplan-Meier curve showing PEP005 and DC therapy synergize to improve cure of primary tumors.

This experiment essentially constitutes a repeat of Example 2 although the average size of the tumors at treatment initiation was larger; the means for each group ranged from 26-30 mm². The DC+IL-2 therapy gave a marginal, but significant improvement in survival times compared to Controls (log rank statistic p=0.0016; FIG. 8). The addition of PEP005 treatment to the DC+IL-2 therapy resulted in an improvement that approached significance (p=0.0508, PEP005+DC+IL-2 vs DC+IL-2). The addition of B16/M720 treatment (PEP005+DC+IL-2+M720/B16) conveyed no advantage. Although PEP005+DC+IL-2 treatment appeared to better than PEP005 treatment alone, this did not reach significance.

Figure 9:
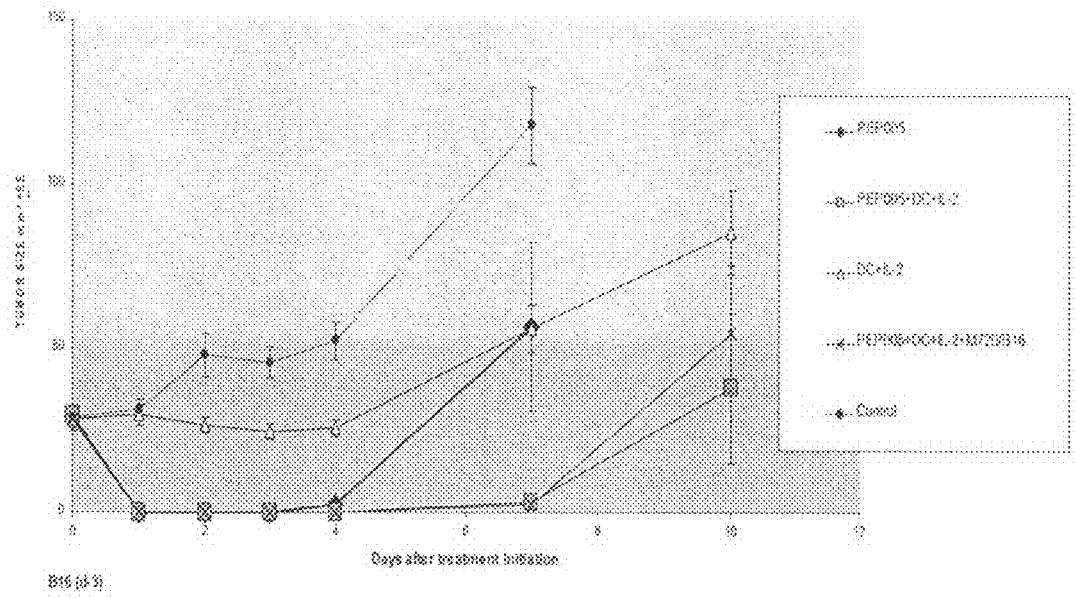
FIG. 9 is a graphical representation of a growth curve for the same experiment shown in FIG. 8. Each line terminates when the first animal in that group is culled as tumors reach 100 mm².

Comparisons of growth curves (FIG. 9) again indicated that PEP005+DC+IL-2 treatment was better than PEP005 treatment alone, although this did not reach significance.

The experiments suggest that DC+IL2 combined with PEP005 is better than PEP005 treatment alone, although the experiment did not reach significance at the 5% level.

Example 4

PEP005 and DC Therapy Synergize to Reduce Growth of Secondary Tumors

It has previously been established that PEP005-mediated curing of primary tumors can lead to the reduction secondary tumors in a B16-OVA lung metastasis and a s.c. Lewis lung-OVA model. These studies were extended (i) using a model where the model antigen ovalbumin is absent, (ii) using a system where both primary and secondary tumors are established before treatment initiation and (iii) using DC therapy combined with PEP005-mediated curing of primaries, to determine whether the two treatments can improve the anti-cancer effect on the secondary tumors.

On d6, three groups of C57BL/6 mice were inoculated with $1\times10^5$ B16 s.c. on the right hand side of the back (RHS) and $2\times10^4$ s.c. on the left hand side of the back (LHS). A fourth group (Group 4) received only $2\times10^4$ s.c. on the left hand side of the back (LHS). On d0. the groups were given the following treatments:

Group 1 (n=7)
PEP005 RHS: The larger RHS tumors were treated intra-tumorally with 25 µg PEP005 in 50 µl of 5% w/v DMSO in RPMI 1640 supplemented with HEPES 10 mM.

Group 2 (n=7)
PEP005 RHS+DC+IL-2: The large RHS tumors were treated as for Group 1 plus the animals received on d0 DC2.4 cells (i) activated with LPS (for 3 hr incubation at 37° C. using 1 µg/ml E. coli 055:B5, Sigma), (ii) sensitized with TRP-2 peptide, SVYDFFVWL [SEQ ID NO:1] (30 µg/ml 2 hr, 37° C.), (iii) irradiated (5000 rads), washed and then injected i.v. ($4\times10^6$/mouse iv) on d0. The animals also received rhIL-2 at $5\times10^4$ IU given twice daily per mouse from d0 to d4 i.p.

Group 3 (n=7)
CONT TREAT RHS: Mock treatment group; the larger RHS tumors were treated intra-tumorally with 50 µl of 5% w/v DMSO in RPMI1640 supplemented with HEPES 10 mM.

Group 4 (n=5)
NO RHS: This group had no RHS tumor and received no treatment.

Figure 11:
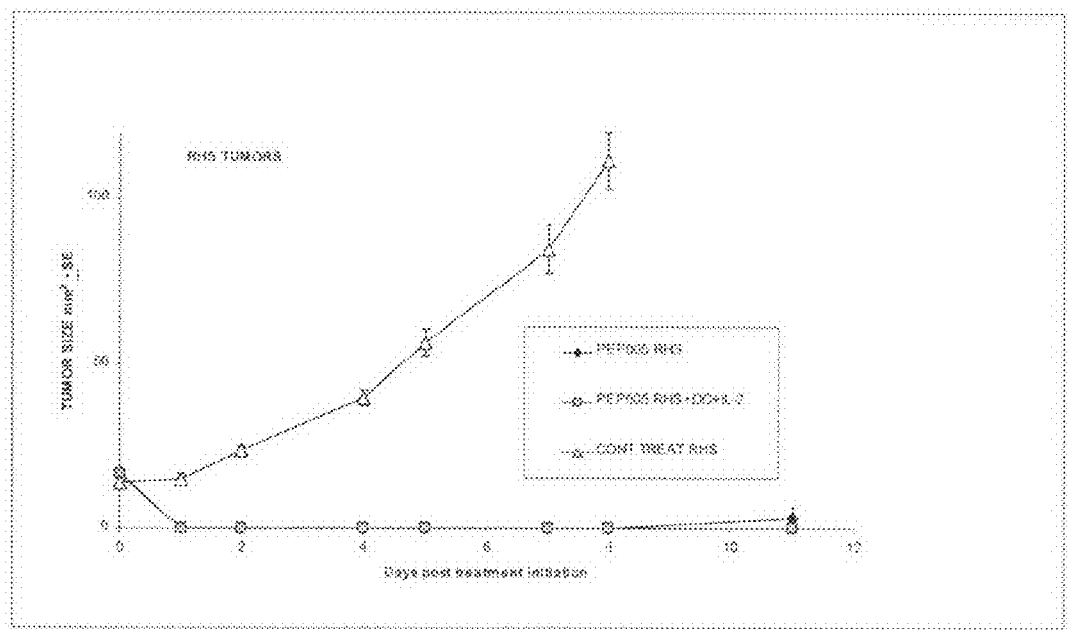
FIG. 11 is a graphical representation of a growth curve for RHS tumor. Each line terminates when the first animal in that group is culled as tumors reach 100 mm².

PEP005 treatment using DMSO was not well tolerated with one mouse in each of Group 1 and 2 dying shortly after i.t. treatment. The RHS tumors were all successfully cured in Group 2 and in Group 1 5/6 animals had their tumors successfully cured with one RHS tumor re-emerging on d11. Mock treatment as expected failed to cure any RHS tumors (CONT TREAT RHS, Group 3, FIG. 11). The presence of a large RHS tumor did not by itself seem to influence the growth of the LHS tumor (FIG. 12, CONT TREAT RHS and NO RHS).

Figure 10:
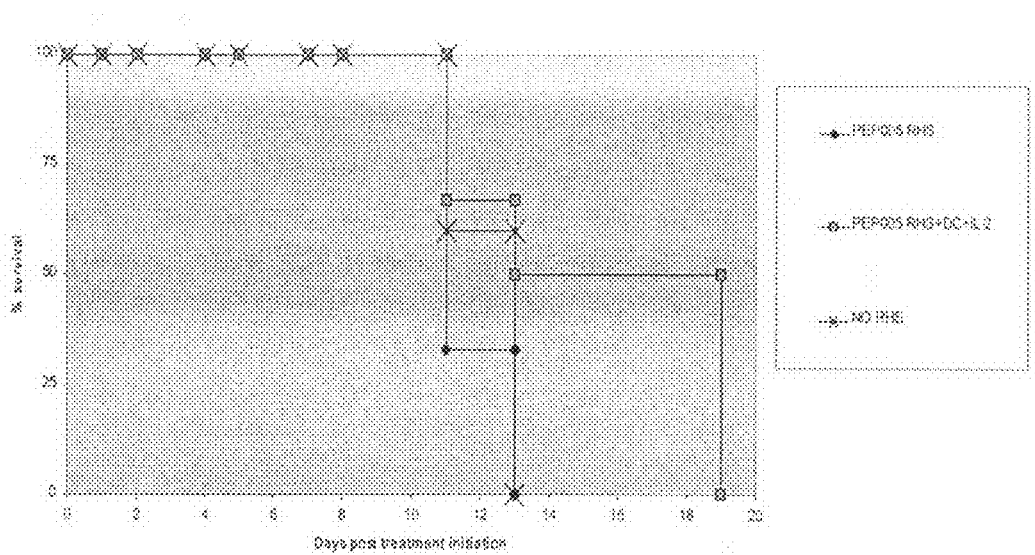
FIG. 10 is a graphical representation of a Kaplan-Meier curve showing PEP005 and DC therapy synergize to reduce growth of secondary tumors. Deaths occur due to growth of secondary tumors. (Group 3 not included.)

Deaths due to growth of the smaller LHS is shown in a Kaplan Meier graph (FIG. 10). The PEP005 RHS group and the NO RHS group behaved essentially identically and for statistical purposed were combined. The PEP005 RHS+DC+IL-2 group provided significantly better survival than the combined PEP005 RHS/NO RHS groups (log rank statistic p=0.048).

Figure 12:
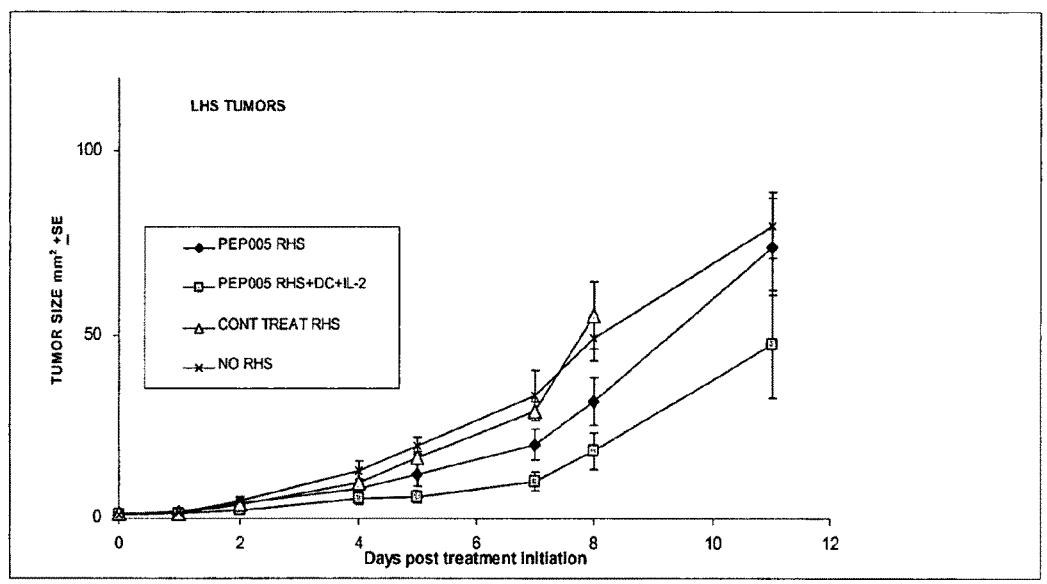
FIG. 12 shows growth curves for the smaller LHS tumors. Each line terminates when the first animal in that group is culled as tumors reach 100 mm². CONT TREAT RHS are culled due to growth of primaries, the rest due to growth of secondaries.

Growth curves for the LHS tumors in the four groups are shown in FIG. 12. From d5 to d11 the tumors in the PEP005 RHS+DC+IL-2 group were significantly smaller than those in the PEP005 RHS group (p=0.014, using one way ANOVA, which included a term for each day, i.e. n=24 for each group). A similar comparison between PEP005 RHS and NO RHS also showed significance (p=0.042), indicating that the growth of the smaller LHS tumor was slower if a larger RHS tumor was cured by i.t. PEP005 treatment.

The experiments illustrated that a smaller secondary tumor (LHS) grows more slowly if a larger primary tumor (RHS) is cured by PEP005 treatment. Accordingly, the curing of a primary tumor by i.t. PEP005 contributed to the slowing of growth of secondary tumors.

When PEP005 treatment of the RHS tumors was combined with DC+IL-2 therapy, the growth of the smaller secondary LHS tumors was slower over d5-d11 than in animals where the RHS tumor received only PEP005 treatment, and no DC+IL-2 (FIG. 12, PEP005 RHS+DC+IL-2 and PEP005 RHS, p=0.014). Thus the additional treatment with DC+IL-2 on top of the PEP005-mediated curing of the RHS primaries provides significant additional reduction in the size of secondary LHS tumors. The latter conclusion is supported by the Kaplan Meier analysis where the PEP005 RHS+DC+IL-2 group survived significantly longer than the combined PEP005 RHS/NO RHS groups (FIG. 10, p=0.048).

Example 5

Synergy Between PEP005 Cure of "Primary" Tumors and DC Therapy for Regression of "Secondary" Tumors DC2.4 Therapy
The DC2.4 cell line is a dendritic cell line derived from C57BL/6 (Shen et al, *J Immunol* 158:2723-2730, 1997), which has been loaded with model cancer antigens and used as DC therapy in several mouse models (Indrova et al, *Folia Biol (Praha* 50:184-193, 2004; Ni et al, *J Neurooncol* 51:1-9, 2001; Brown et al, *Gene Ther* 7:1680-1689, 2000; Okada et al, *Cancer Res* 61:7913-7919, 2001). It was confirmed that maturation of peptide-pulsed DC2.4 cells with lipopolysaccharide and IFNγ (Huttner et al, *Cancer Immunol Immunother* 54:67-77, 2005) significantly enhanced their ability to induce anti-cancer $CD8^+$ T-cell responses. Such matured and irradiated DC2.4 cells pulsed with SVYDFFVWL [SEQ ID NO:1] (Bloom et al, *J Exp Med* 185:453-459, 1997) and given by i.v. ($3\times10^6$ cells/mouse) generated 100-200 epitope specific IFNγ spots/$10^6$ splenocytes as measured by ELISPOT 2-3 weeks post immunization. If IFNγ treatment was omitted these responses dropped to 20-50 IFNγ spots/$10^6$ splenocytes.

DC2.4 cells were pulsed with two $CD8^+$ T-cell epitopes known to stimulate anti-B16 $CD8^+$ T-cell responses; SVYDFFVWL [SEQ ID NO:1], and the human gp100 epitope KVPRNQDWL [SEQ ID NO:4], which is able to stimulate effectively $CD8^+$ T-cells specific for murine gp100 (Lou et al, *Cancer Res* 64:6783-6790, 2004). Peptide pulsed, matured, irradiated and washed DC2.4 cells were used as a therapy for B16 lung metastases.

Figure 13:
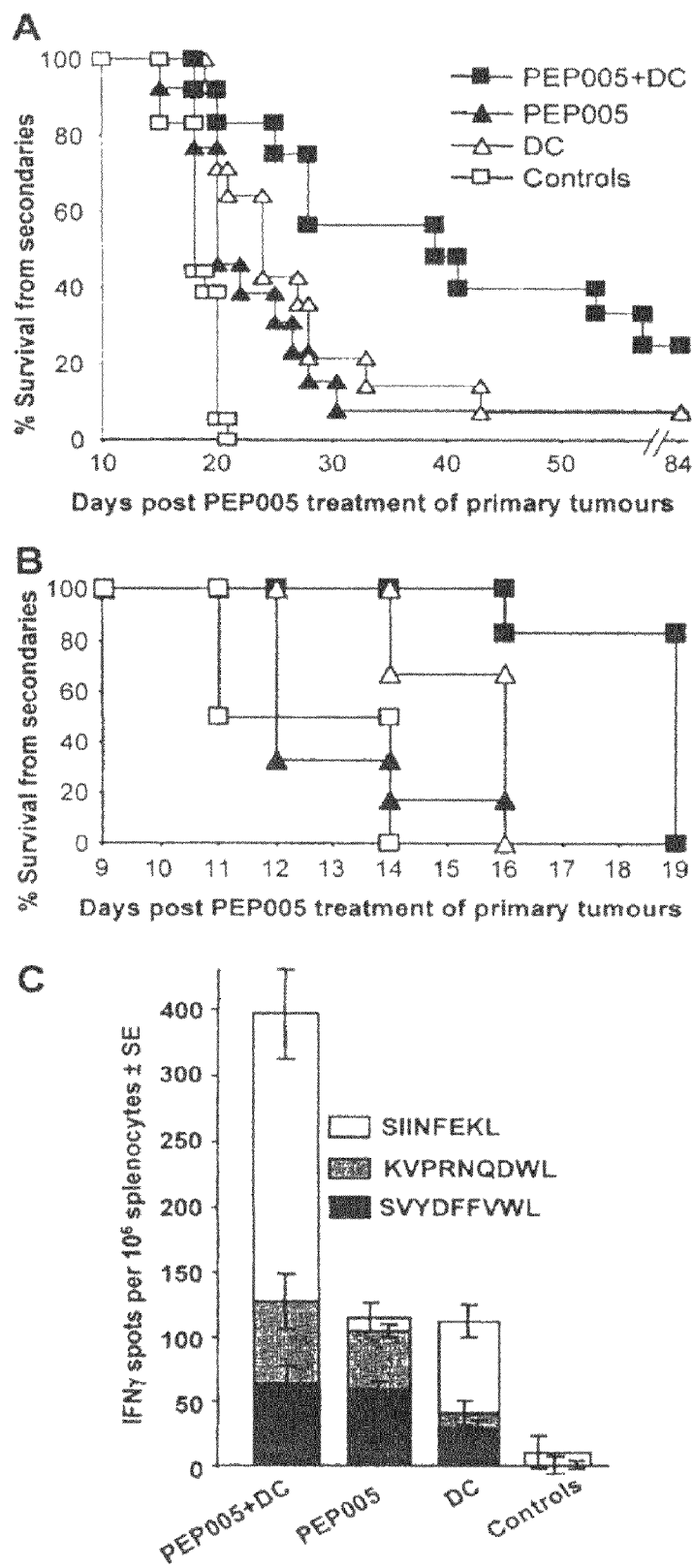
FIGS. 13A to C are graphical representations showing synergistic effects between PEP005-mediated cure of primaries and DC therapy on the growth of secondary tumors and on CD8⁺ T-cell induction. (A) On d−3 C57BL/6 mice where inoculated with $2\times10^6$ B16-OVA cells on the right flank (primary tumor) and $2\times10^4$ B16-OVA cells on the left flank (secondary tumor). On d0 and d1 the primary B16-OVA tumors, which has reach 30.4 mm²+SD6 were cured with i.t. injections of 25 µg of PEP005 formulated in PEG400. On d4 and d11 mice received DC therapy using DC2.4 cells pulsed with SVYDFFVWL [SEQ ID NO:1], KVPRNQDWL [SEQ ID NO:4] and SIINFEKL [SEQ ID NO:2] peptides, and ovalbumin (n=12, PEP005+DC). A second group of mice were treated in the same way (primaries measuring 30 mm²+SD 5.1 on d0), but did not receive the DC therapy (n=13, PEP005). A third group was inoculated with secondary tumors only and received the DC therapy (n=14, DC), and the control group was given only secondary tumors and received no treatment (n=18, Control). Animals were culled when the secondary tumors reached 100 mm². (B) The experiment in (A) was repeated in the B16 model (n=6 per group). On d−2 C57BL/6 mice were inoculated with $10^6$ B16 cells on the right flank (primary tumor) and $5\times10^4$ cells on the left flank (secondary tumors). On d0 the primary tumors had reached 20 mm²+SD 1.9 and were treated on d0 and d1 with PEP005 as above. On d5 and d12 mice received DC2.4 cells pulsed with SVYDFFVWL [SEQ ID NO:1] and KVPRNQDWL [SEQ ID NO:4] (legend as for (A), PEP005+DC). A second group of mice was treated like the first but without DC therapy (PEP005). A third group was inoculated with secondary tumors only and received DC therapy (DC) and the control group was given only secondary tumors and received no treatment (Control). Animals were culled as above. (C) CD8⁺ T-cell induction in the B16-OVA model. Animal groups were established and treated as in (A) except that on d12 mice were sacrificed and splenocytes analyzed in an ex vivo ELISPOT assay for responses to SVYDFFVWL [SEQ ID NO:1], KVPRNQDWL [SEQ ID NO:4] and SIINFEKL [SEQ ID NO:2] (n=6 per group).

Synergy Between PEP005-Mediated Cure of Primary Tumors and DC Therapy to Reduce Growth of Secondaries To determine whether the immunostimulatory activity of PEP005-mediated cure of primary tumors would synergize with DC therapy to reduce growth of secondaries, four groups of C57BL/6 mice were established using the s.c. B16-OVA model. In the first group nominal s.c. primary and smaller s.c. secondary tumors were implanted at the same time. When the primary tumors reached a mean of 30 mm² they were cured with PEP005 treatment, and the mice received DC therapy (FIG. 13A, PEP005+DC). The second group was like the first except that DC therapy was omitted (FIG. 13A, PEP005). In the third group only secondary tumors were established and mice were given the same DC therapy as the first group (FIG. 13A, DC). The fourth group only had secondary tumors and received no treatment (FIG. 13A, Controls). The growth of secondary tumors was monitored over time. The combination of curing the primary tumors with PEP005 plus DC therapy showed significantly greater anti-cancer activity against the secondary tumors than PEP005-mediated cure of primaries alone or DC therapy alone (Log rank statistic p=0.02 and 0.049, respectively). Individually, PEP005-mediated cure of primaries and DC therapy both significantly reduced the growth of secondaries when compared to the no treatment controls (Log rank statistic p<0.001 and =0.002, respectively) (FIG. 13A).

Using the more aggressive B16 model, a comparable experiment to that shown above was undertaken. Again curing of primary tumors with PEP005 combined with DC therapy gave significantly delayed growth of secondaries compared to either treatment alone (p=0.001 and 0.046, respectively) (FIG. 13B). DC therapy alone again significantly reduced the growth of secondaries compared to the no treatment controls (p=0.009), although curing of primaries with PEP005 alone in this model did not provide a significant delay of tumor growth compared with controls.

These experiments illustrated that PEP005-mediated cure of the larger primaries synergized with DC therapy to regress the smaller secondary tumors. In other words, DC therapy was significantly more effective against secondaries in animals where the primary tumors had been cured with PEP005 treatment, than it was in animals where the primary tumor was absent.

Synergistic Activity Against Secondaries of Combined PEP005 and DC Therapies Correlates with Anti-Cancer $CD8^+$ T-Cell Induction To determine whether the synergistic effect of PEP005 and DC therapies seen in FIG. 3A correlated with anti-cancer $CD8^+$ T-cell induction, a group of animals were established and treated as described for FIG. 13A except the animals were killed on d12 and their splenocytes analyzed for B16-OVA-specific $CD8^+$ T-cells responses. B16-OVA-specific $CD8^+$ T-cells are known to recognize the Trp-2 epitope (Zeh et al, 1999 supra) SVYDFFVWL [SEQ ID NO:1], the gp100 epitope KVPRNQDWL [SEQ ID NO:4] (Lou et al, 2004 supra) and the ovalbumin epitope SIINFEKL [SEQ ID NO:2]. The combined PEP005 plus DC therapy induced ≈400 spots/$10^6$ splenocytes of B16-OVA-specific $CD8^+$ T-cell responses (FIG. 13C, PEP005+DC), whereas PEP005-mediated cure and DC therapy individually each only induced about 120 spots/$10^6$ splenocytes (FIG. 13C, PEP005 and DC, respectively). In the absence of treatment no significant B16-OVA-specific $CD8^+$ T-cell responses were detected (FIG. 13C, Controls). These data suggest that the synergistic therapeutic activity of PEP005 plus DC treatment is due to synergistic induction of anti-cancer $CD8^+$ T-cells.

Conclusions

DC therapy and other immune-based therapies attempting to generate anti-cancer $CD8^+$ T-cells usually perform better when the overall tumor burden is low. Reducing the tumor burden is thus desirable before initiating such immune-based therapy. However, reducing the tumor burden with conventional chemotherapy runs the risk of immunosuppression resulting in the immunotherapy being compromised.

It is shown here that PEP005-mediated cure of established cancers induced anti-cancer T-cells, which were able to regress distant tumors. Furthermore, the PEP005-mediated cure synergized with $DC8^+$ T-cell-based cancer vaccines to promote anti-cancer activity against secondary tumors. Thus local PEP005 treatment emerges as a novel chemotherapy that can be used in conjunction with immune-based therapies to both reduce the tumor burden and to stimulate anti-cancer $CD8^+$ T-cell activity.

Example 6

Combining PEP005-Mediated Curing of Primary Tumors with Peptide Vaccination in the CT26 Colon Carcinoma Model Materials and Methods
CT26 Tumors
CT26 colon carcinoma cells [CRL-2638] (Ali et al, 2002 supra) were grown s.c. in 6-10 week old female Balb/c mice.

Cancer Vaccine
The cancer vaccine comprised the gp70 A-1 peptide epitope SPSYVYHQF [SEQ ID NO:5] (Ali et al, 2002 supra) and ovalbumin (as a source of CD4 T-cell help) dissolved in RPMI 1640 emulsified with Montanide ISA 51 VG (Seppic, Paris, France) (at a ratio of 3:7 vol:vol), and injected s.c. Each 100 μl immunization contained 50 μg peptide and 10 μg ovalbumin.

Figure 14:
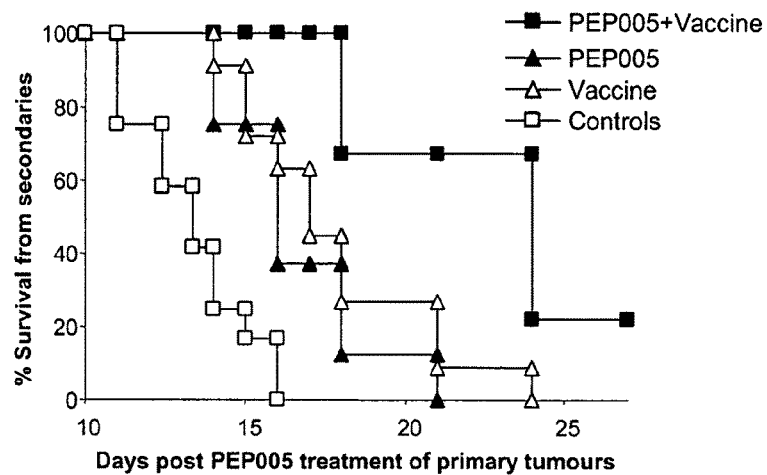
FIG. 14 is a graphical representation combining PEP005-mediated cure of primaries and cancer vaccination in the CT26 colon carcinoma model. (A) on d−3 C57BL/6 mice were inoculated with $10^5$ CT26 cells on the left flank (primary tumor) and $5\times10^3$ CT26 cells on the right flank (secondary tumor). On d0 the primary CT26 tumors, which has reached 16.8+SD 3.2 mm² were cured with i.t. injections of 25 µg of PEP005 formulated in PEG400. On d3 and d10 mice received peptide vaccine containing the SPSYVYHQF [SEQ ID NO:5] epitope (n=9, PEP005+Vaccine). Second group of mice were treated in the same way (primaries measuring 17.5+SD 2.1 mm² on d0), but did not receive the vaccine (n=8, PEP005). A third group was inoculated with secondary tumors only and received the vaccine (n=11, Vaccine), and the control group was given only secondary tumors and received no treatment (n=12, Controls). Animals were culled when the secondary tumors reached 100 mm².

Results
To determine whether the effects seen in the B16 models could be repeated in a different tumor model and using a different cancer vaccine, four groups of Balb/c mice were established using the CT26 colon carcinoma model (Ali et al, J Immunol 168:3512-3519, 2002). In the first group nominal s.c. primary and smaller s.c. secondary tumors were implanted at the same time. The primary tumors were cured with PEP005 treatment and the mice also received the peptide vaccine (FIG. 14, PEP005+Vaccine). The second group was like the first except that vaccine was omitted (FIG. 14, PEP005). In the third group only secondary tumors were established and mice were given the same vaccine as the first group (FIG. 14, Vaccine). The fourth group only had secondary tumors and received no treatment (FIG. 14, Controls). The growth of secondary tumors was monitored as above. The combination of curing the primary tumors with PEP005 plus Vaccine showed significantly greater anti-cancer activity against the secondary tumors than PEP005-mediated cure of primaries alone or Vaccine alone (Log rank statistic p=0.003 and <0.001, respectively). Individually, PEP005-mediated cure of primaries and Vaccine both significantly reduced the growth of secondaries when compared to the no treatment controls (Log rank statistic p=0.011 and =0.013, respectively) (FIG. 14).

Conclusions
Thus in a second tumor model (CT26) and using an alternative vaccination modality (Montanide ISA 51) to induce cancer-specific $CM^+$ T-cells, PEP005-mediated cure of primaries was able to synergize with the cancer vaccine to decrease the growth of secondary tumors.

Example 7

Induction of Anti-Cancer Antibodies by PEP005 Treatment

Figure 15:
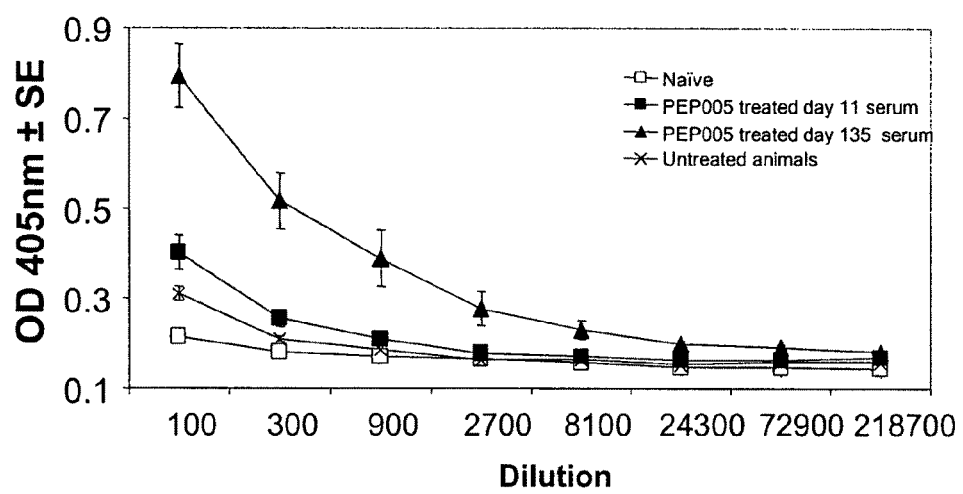
FIG. 15 is a graphical representation showing antibody responses following PEP005 treatment of B16 tumors. B16 tumors growing on C57BL/6 mice were cured with PEP005 treatment after they had reached 30-60 mm³, (one tumor per mouse) and B16-specific antibody titers were measured by standard ELISA on blood taken d11 post treatment initiation (n=6) (■) or d135 post treatment initiation (n=5) (▲). Antibody titers for untreated animals whose tumors had reached 121.5±SD 20.1 (n=4) by d11 are also shown (X). Naïve mice (n=5) received no tumors (i).

Introduction and Results
Anti-tumor antibodies are known to have anti-cancer activity. PEP005 treatment of B16 tumors induced clearly detectable antibody responses in C57BL/6 mice as early as d11, with responses at this time point even exceeding those in untreated animals with large tumor burdens (FIG. 15, p=0.045 at 1/100 dilution, unpaired Student's t-test). B16 cells ($10^6$) were injected s.c. (1 tumor/mouse) into the flanks of female, 6-10 week-old mice and when tumors had reached ≈30-60 mm$^3$ they were treated with PEP005 as above. On d11 and 135 serum was taken and analyzed by ELISA for antibodies specific for B16. A group of B16 bearing animals which were not treated with PEP005 and a naïve group were also included. B16 cells were sonicated in carbonate buffer 9pH=9) and absorbed onto Immuno Maxisorp 96 well plates (Nunc) overnight and dried. The plates were blocked with 5% v/v FBS, 0.01% v/v Tween in PBS for 1 hour at 37° C. Test sera were serially diluted in duplicate and probed with rat-mouse biotinylated primary antibody (BD Biosciences Pharmingen) and HRP-labeled streptavidin (Biosource International, Camarillo, Calif.) followed by ABTS substrate (Sigma) and measurement of OD at 405 nm.

Conclusions

The induction of anti-cancer antibodies by PEP005 treatment suggests that antibody induction may contribute to tumor killing. The induction of IgG responses provides compelling evidence that PEP005 treatment induces cancer-specific CD4 T-cells. That CD4 T-cells are induced is also supported by the fact that CD8+ T-cells are effectively induced by PEP005 treatment.

Those skilled in the art will appreciate that the invention described herein is susceptible to variations and modifications other than those specifically described. It is to be understood that the invention includes all such variations and modifications. The invention also includes all of the steps, features, compositions and compounds referred to or indicated in this specification, individually or collectively, and any and all combinations of any two or more of said steps or features.

BIBLIOGRAPHY

Ali et al, *J Immunol* 168:3512-3519, 2002
Basak et al, *Viral Immunol. Summer* 17(2):182-96, 2004
Bloom et al, *J. Exp. Med.* 185:453-459, 1997
Brown et al, *Gene Ther* 7:1680-1689, 2000
Camporeale et al, *Can Res* 63:3688, 2003
Elliott et al, *Vaccine.* 17(15-16):2009-2019, 1999
Huttner et al, *Cancer Immunol Immunother* 54:67-77, 2005
Indrova et al, *Folia Biol (Praha)* 50:184-183, 2004
Le et al, *Vaccine* 19:4669-4675, 2001
Lenarczyk et al, *Vaccine* 22:963-974, 2004
Lonchay et al, *Proc Natl Acad Sci USA.* 101 Suppl 2:14631-8, 2004
Lou et al, *Cancer Res* 64:6783-6790, 2004
McAllister et al, *J. Virol* 74:9197-9205, 2000
Machlenkin et al, *Clin Cancer Res* 11:4955-4961, 2005
Maraskovsky et al, *Clin Cancer Res.* 10(8):2879-90, 2004
Morcellin et al, *Lancet Oncol* 5:681-689, 2004
Nelson et al, *J Immunol.* 166:5557-66, 2001
Ni et al, *Neurooncol.* 51:1-9, 2001
Ogbourne et al, *Cancer Research* 64:2833-2839, 2004
Okada et al, *Cancer Res* 61:7913-7919, 2001
Shen et al, *J. Immunol.* 158:2723-2730, 1997
Thomson et al, *J Immunol* 157:822-826, 1996
Zeh et al, *J Immunol* 162:989-994, 1999

The invention claimed is:

1. A method for treating a secondary cancer in a subject, said method comprising administering isolated or purified ingenol-3-angelate or a pharmaceutically acceptable salt thereof topically and/or intra-tumorally to a primary cancer on the skin of said subject in an amount effective to induce primary necrosis in at least the cancer cells and to stimulate the generation of anti-cancer-specific T-cells wherein said subject has a secondary cancer.

2. The method of claim 1 wherein the cancer-specific T-cell is a $CD8^+$ T-cell or a precursor or subset thereof.

3. The method of claim 1 wherein the cancer-specific T-cell is a $CD4^+$ T-cell or a precursor or subset thereof.

4. The method of claim 1 further comprising using the administration of an agent or therapy which enhances, co-operates or synergizes with the cancer-specific T-cells induced following treatment with the ingenol-3-angelate.

5. The method of claim 1 wherein said ingenol-3-angelate is derived from a plant of the Euphorbiaceae family or botanical or horticultural relatives of such plants.

6. The method of claim 5 wherein the ingenol-3-angelate is derived from *E. peplus*.

7. The method of claim 4 wherein said agent is a cancer vaccine.

8. The method of claim 4 wherein said agent is a cytokine or cocktail of cytokines.

9. The method of claim 8 wherein the cytokine is IL-2, IL-7 and/or IL-15.

10. The method of claim 7 wherein the cancer vaccine is a DC vaccine.

11. The method of claim 7 wherein the cancer vaccine comprises a cancer vaccine containing or encoding a cancer antigen or epitope.

12. The method of claim 1 wherein the cancer is selected from the list consisting of AIDS related cancer, acoustic neoma, adenocystic carcinoma, adrenocortical cancer, agnogenic myeloid metaplasia, alopecia, alveolar soft-part sarcoma, anal cancer, angiosarcoma, aplastic anaemia, astrocytoma, ataxia-telangiectasia, basal cell carcinoma (bcc), bladder cancer, bone cancers, bowel cancer, brain stem glioma, brain and CNS cancers, breast cancer, CNS cancers, carcinoid cancers, cervical cancer, childhood brain cancers, childhood cancer, childhood soft tissue sarcoma, chondrosarcoma, choriocarcinoma, colorectal cancers, cutaneous T-Cell lymphoma, dermatofibrosarcoma-protuberans, desmoplastic small round cell cancer, ductal carcinoma, endocrine cancers, endometrial cancer, ependymoma, esophageal cancer, Ewing's sarcoma, extra hepatic bile duct cancer, eye cancer, eye: melanoma, retinoblastoma, fallopian tube cancer, fanconi anaemia, fibrosarcoma, gall bladder cancer, gastric cancer, gastrointestinal cancers, gastrointestinal carcinoid cancer, genitourinary cancers, germ cell cancers, gestational trophoblastic disease, glioma, gynecological cancers, hematological malignancies, head and neck cancer, hepatocellular cancer, hereditary breast cancer, histiocytosis, Hodgkin's disease, human papillomavirus, hydatidiform mole, hypercalcemia, hypopharynx cancer, intra-ocular melanoma, isle T-cell cancer, Kaposi's sarcoma, kidney cancer, Langerhan's cell histiocytosis, laryngeal cancer, leiomyosarcoma, li-fraumeni syndrome, lip cancer, liposarcoma, liver cancer, lung cancer, lymphedema, lymphoma, Hodgkin's lymphoma, non-Hodgkin's lymphoma, male breast cancer, malignant rhabdoid cancer of kidney, medulloblastoma, melanoma, merkel cell cancer, mesothelioma, metastatic cancer, mouth cancer, multiple endocrine neoplasia, mycosis fungoides, myelodysplastic syndromes, myeloma, myeloproliferative disorders, nasal cancer, nasopharyngeal cancer, nephroblastoma, neuroblastoma, neurofibromatosis, nijmegen breakage syndrome, non-melanoma skin cancer, non-small cell lung cancer (nscic), ocular cancers, oesophageal cancer, oral cavity cancer, oropharynx cancer, osteosarcoma, ostomy ovarian cancer, pancreas cancer, paranasal cancer, parathyroid cancer, parotid gland cancer, penile cancer, peripheral neuroectodermal cancers, pituitary cancer, polycythemia vera, prostate cancer, rare cancers and associated disorders, renal cell carcinoma, retinoblastoma, rhabdomyosarcoma, rothmund Thomson syndrome, salivary gland cancer, sarcoma, schwannoma, sezary syndrome, skin cancer, small cell lung cancer (scic), small intestine cancer, soft tissue sarcoma, spinal cord cancers, squamous cell carcinoma (scc), stomach cancer, synovial sarcoma, testicular cancer, thymus cancer, thyroid cancer, transitional cell cancer (bladder), transitional cell cancer (renal-pelvis-/-ureter), trophoblastic cancer, urethral cancer, urinary system cancer, uroplakins, uterine sarcoma, uterus cancer, vaginal Cancer, vulva cancer, Waldenstrom's macroglobulinemia and Wilms' Cancer.

13. The method of claim 12 wherein the cancer is selected from lung cancer, breast cancer, colon cancer and bladder cancer.

14. The method according to claim 1 wherein said purified or isolated ingenol-3-angelate or said pharmaceutically acceptable salt thereof is not administered directly to said secondary cancer.

* * * * *

SEQUENCE LISTING

```
<160> NUMBER OF SEQ ID NOS: 5

<210> SEQ ID NO 1
<211> LENGTH: 9
<212> TYPE: PRT
<213> ORGANISM: Artificial Sequence
<220> FEATURE:
<223> OTHER INFORMATION: synthetic peptide: Dominant Trp2 CD8+ T-cell
      epitope for anti-B/6 CD8+ T-cells

<400> SEQUENCE: 1

Ser Val Tyr Asp Phe Phe Val Trp Leu
1               5

<210> SEQ ID NO 2
<211> LENGTH: 8
<212> TYPE: PRT
<213> ORGANISM: Artificial Sequence
<220> FEATURE:
<223> OTHER INFORMATION: synthetic peptide: CD8+ T-cell epitope for
      ovalbumin

<400> SEQUENCE: 2

Ser Ile Ile Asn Phe Glu Lys Leu
1               5

<210> SEQ ID NO 3
<211> LENGTH: 9
<212> TYPE: PRT
<213> ORGANISM: Artificial Sequence
<220> FEATURE:
<223> OTHER INFORMATION: synthetic peptide: Trp-2 epitope (human)

<400> SEQUENCE: 3

Lys Val Tyr Arg Asn Gln Asp Trp Leu
1               5

<210> SEQ ID NO 4
<211> LENGTH: 9
<212> TYPE: PRT
<213> ORGANISM: Artificial Sequence
<220> FEATURE:
<223> OTHER INFORMATION: synthetic peptide: human gp100 epitope
```

```
<400> SEQUENCE: 4

Lys Val Pro Arg Asn Gln Asp Trp Leu
1               5

<210> SEQ ID NO 5
<211> LENGTH: 9
<212> TYPE: PRT
<213> ORGANISM: Artificial Sequence
<220> FEATURE:
<223> OTHER INFORMATION: synthetic peptide: Epitope on CT26 colon
      carcinoma cells

<400> SEQUENCE: 5

Ser Pro Ser Tyr Val Tyr His Gln Phe
1               5
```